US012207887B1

(12) United States Patent
Barral et al.

(10) Patent No.: US 12,207,887 B1
(45) Date of Patent: Jan. 28, 2025

(54) SYSTEMS AND METHODS FOR DETECTING DELAYS DURING A SURGICAL PROCEDURE

(71) Applicant: Verily Life Sciences LLC, South San Francisco, CA (US)

(72) Inventors: Joëlle Barral, Mountain View, CA (US); Martin Habbecke, Palo Alto, CA (US); Xing Jin, San Jose, CA (US); Caitlin Donhowe, Mountain View, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 1031 days.

(21) Appl. No.: 16/947,810

(22) Filed: Aug. 18, 2020

Related U.S. Application Data

(60) Provisional application No. 62/888,773, filed on Aug. 19, 2019.

(51) Int. Cl.
*G16H 70/20* (2018.01)
*A61B 34/00* (2016.01)
(Continued)

(52) U.S. Cl.
CPC .............. *A61B 34/20* (2016.02); *A61B 34/25* (2016.02); *A61B 34/30* (2016.02); *A61B 90/37* (2016.02); *G06T 7/0012* (2013.01); *G06V 20/20* (2022.01); *G06V 20/41* (2022.01); *G08B 5/36* (2013.01); *G08B 21/182* (2013.01); *G16H 50/20* (2018.01); *G16H 70/20* (2018.01); *H04L 51/046* (2013.01); *H04W 4/14* (2013.01);
(Continued)

(58) Field of Classification Search
None
See application file for complete search history.

(56) References Cited

U.S. PATENT DOCUMENTS 9,171,477 B2 10/2015 Luo et al.
9,788,907 B1 10/2017 Alvi et al.
(Continued)

FOREIGN PATENT DOCUMENTS

CN 109147254 1/2019
WO 2016200887 12/2016
(Continued)

OTHER PUBLICATIONS

U.S. Appl. No. 16/736,467, Notice of Allowance, Mailed on Oct. 20, 2022, 11 pages.
(Continued)

*Primary Examiner* — Idowu O Osifade
(74) *Attorney, Agent, or Firm* — Kilpatrick Townsend & Stockton LLP

(57) ABSTRACT

Examples of systems and methods for detecting delays during a surgical procedure are disclosed. For example, one disclosed method includes receiving, a computing device, video of a robotic surgical procedure; determining, by the computing device, an estimated time-to-complete ("TTC") the robotic surgical procedure based on the video; and in response to determining a deviation between the estimated TTC and an expected duration of the robotic surgical procedure exceeds a threshold, outputting an indication that the robotic surgical procedure is deviating from the expected duration.

27 Claims, 11 Drawing Sheets

(51) Int. Cl.

| | |
|---|---|
| *A61B 34/20* | (2016.01) |
| *A61B 34/30* | (2016.01) |
| *A61B 90/00* | (2016.01) |
| *G06T 7/00* | (2017.01) |
| *G06V 20/20* | (2022.01) |
| *G06V 20/40* | (2022.01) |
| *G08B 5/36* | (2006.01) |
| *G08B 21/18* | (2006.01) |
| *G16H 50/20* | (2018.01) |
| *H04L 51/046* | (2022.01) |
| *H04W 4/14* | (2009.01) |

(52) U.S. Cl.
CPC .. *A61B 2034/2055* (2016.02); *A61B 2034/301* (2016.02); *A61B 2034/742* (2016.02); *G06T 2207/10016* (2013.01); *G06T 2207/30004* (2013.01); *G06V 2201/03* (2022.01)

(56) References Cited

U.S. PATENT DOCUMENTS

| | | | |
|---|---|---|---|
| 9,836,654 | B1 | 12/2017 | Alvi et al. |
| 2010/0088726 | A1 | 4/2010 | Curtis et al. |
| 2011/0046476 | A1 | 2/2011 | Cinquin et al. |
| 2014/0220527 | A1 | 8/2014 | Li et al. |
| 2014/0286533 | A1 | 9/2014 | Luo et al. |
| 2015/0005622 | A1 | 1/2015 | Zhao et al. |
| 2017/0132785 | A1 | 5/2017 | Wshah et al. |
| 2019/0069957 | A1* | 3/2019 | Barral .............. A61B 34/20 |
| 2019/0090969 | A1 | 3/2019 | Jarc et al. |
| 2019/0188567 | A1 | 6/2019 | Yao et al. |
| 2019/0223961 | A1 | 7/2019 | Barral et al. |
| 2020/0126661 | A1 | 4/2020 | Flexman et al. |
| 2020/0175265 | A1 | 6/2020 | Schön et al. |
| 2020/0226751 | A1 | 7/2020 | Jin et al. |
| 2020/0237452 | A1* | 7/2020 | Wolf .................. G06F 3/048 |

FOREIGN PATENT DOCUMENTS

| | | |
|---|---|---|
| WO | 2017076221 | 5/2017 |
| WO | 2017083768 | 5/2017 |
| WO | 2018219551 | 12/2018 |

OTHER PUBLICATIONS

Jin et al., "EndoRCN: Recurrent Convolutional Networks for Recognition of Surgical Workflow in Cholecystectomy Procedure Video", Institute of Electrical and Electronics Engineers, 2016, 4 pages.

Haro et al., "Surgical Gesture Classification from Video Data", International Conference on Medical Image Computing and Computer-Assisted Intervention, Part I, Springer, LNCS, vol. 7510, Oct. 2012, pp. 34-41.

Lin et al., "Automatic Detection and Segmentation of Robot-Assisted Surgical Motions", International Conference on Medical Image Computing and Computer-Assisted Intervention, Springer, LNCS, vol. 3749, No. 9, Feb. 2005, 8 pages.

Padoy et al., "A Boosted Segmentation Method for Surgical Workflow Analysis", International Conference on Medical Image Computing and Computer-Assisted Intervention, Part I, Springer, LNCS, vol. 4791, Nov. 2007, pp. 102-109.

International Application No. PCT/US2020/012740, International Search Report and Written Opinion, Mailed on May 20, 2020, 17 pages.

International PCT/US2020/012740, "Invitation to Pay Additional Fees and, Where Applicable, Protest Fee", Mar. 5, 2020, 2 pages.

Subetha et al., "A Survey on Human Activity Recognition from Videos", International Conference on Information Communication and Embedded Systems (ICICES), Feb. 2016, 7 pages.

Tao et al., "Surgical Gesture Segmentation and Recognition", International Conference on Medical Image Computing and Computer-Assisted Intervention, Springer, LNCS, vol. 8151, Sep. 2013, pp. 1-8.

Twinanda et al., "EndoNet: A Deep Architecture for Recognition Tasks on Laparoscopic Videos", IEEE Transactions on Medical Imaging, vol. 36, No. 1, 2016, pp. 1-11.

Volkov et al., "Machine Learning and Coresets for Automated Real-Time Video Segmentation of Laparoscopic and Robot-Assisted Surgery", IEEE International Conference on Robotics and Automation (ICRA), 2017, 6 pages.

Zappella et al., "Surgical Gesture Classification from Video and Kinematic Data", Medical Image Analysis, vol. 17, Oct. 2013, pp. 732-745.

U.S. Appl. No. 16/736,467, Non-Final Office Action, mailed Nov. 17, 2021, 26 pages.

Jin et al., "SV-RCNet: Workflow Recognition From Surgical Videos Using Recurrent Convolutional Network", IEEE Transactions on Medical Imaging, vol. 37, Issue 5, May 2018, pp. 1114-1126.

U.S. Appl. No. 16/736,467, Final Office Action, Mailed on May 20, 2022, 35 pages.

Dergachyova et al., "Automatic Data-Driven Real-Time Segmentation and Recognition of Surgical Workflow", International journal of computer assisted radiology and surgery, vol. 11, No. 6, Apr. 2016, 16 pages.

U.S. Appl. No. 18/154,070 , "Non-Final Office Action", filed Oct. 13, 2023, 10 pages.

U.S. Appl. No. 18/154,070 , "Final Office Action", filed Feb. 5, 2024, 7 pages.

U.S. Appl. No. 18/154,070 , "Notice of Allowance", filed Jul. 9, 2024, 8 pages.

* cited by examiner

SYSTEMS AND METHODS FOR DETECTING DELAYS DURING A SURGICAL PROCEDURE

CROSS-REFERENCE TO RELATED APPLICATIONS

This application claims priority to U.S. Provisional Patent Application No. 62/888,773, filed Aug. 19, 2019, titled "Systems and Methods for Detecting Delays During a Surgical Procedure," the entirety of which is hereby incorporated by reference.

FIELD

The present application generally relates to processing surgical video and more particularly relates to systems and methods for detecting delays during a surgical procedure.

BACKGROUND

Surgical procedures are typically scheduled by a hospital to last a predetermined period of time, based on the type of procedure and the amount of time such procedures have taken in the past. This information is used to schedule successive surgeries in the same operating room ("OR") or to plan a surgeon's schedule to perform multiple surgeries over the course of a day or several days. When a surgery runs longer than expected, such as due to a complication, it impacts any subsequently scheduled surgeries involving the same personnel or the same operating room. However, determining whether a surgery is on schedule or not can be hard to tell and further, the fact that a surgery is taking longer than expected may not be made apparent immediately. In some instances, that a surgery is running long may only be noticed by the patient's family, other medical teams to use a particular operating room, or a hospital administrator who periodically checks on surgery status.

SUMMARY

Various examples are described for systems and methods for detecting delays during a surgical procedure. One example method includes receiving, a computing device, video of a robotic surgical procedure; determining, by the computing device, an estimated time-to-complete ("TTC") the robotic surgical procedure based on the video; and in response to determining a deviation between the estimated TTC and an expected duration of the robotic surgical procedure exceeds a threshold: outputting an indication that the robotic surgical procedure is deviating from the expected duration.

One example system includes a non-transitory computer-readable medium; and a processor communicatively coupled to the non-transitory computer-readable medium, the processor configured to execute processor-executable instructions stored in the non-transitory computer-readable medium to: receive video of a robotic surgical procedure; determine an estimated time-to-complete ("TTC") the robotic surgical procedure based on the video; and in response to a determination of a deviation between the estimated TTC and an expected duration of the robotic surgical procedure exceeds a threshold: output an indication that the robotic surgical procedure is deviating from the expected duration.

One example includes a non-transitory computer-readable medium comprising processor-executable instructions configured to cause a processor to: receive video of a robotic surgical procedure; determine an estimated time-to-complete ("TTC") the robotic surgical procedure based on the video; and in response to a determination of a deviation between the estimated TTC and an expected duration of the robotic surgical procedure exceeds a threshold: output an indication that the robotic surgical procedure is deviating from the expected duration.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
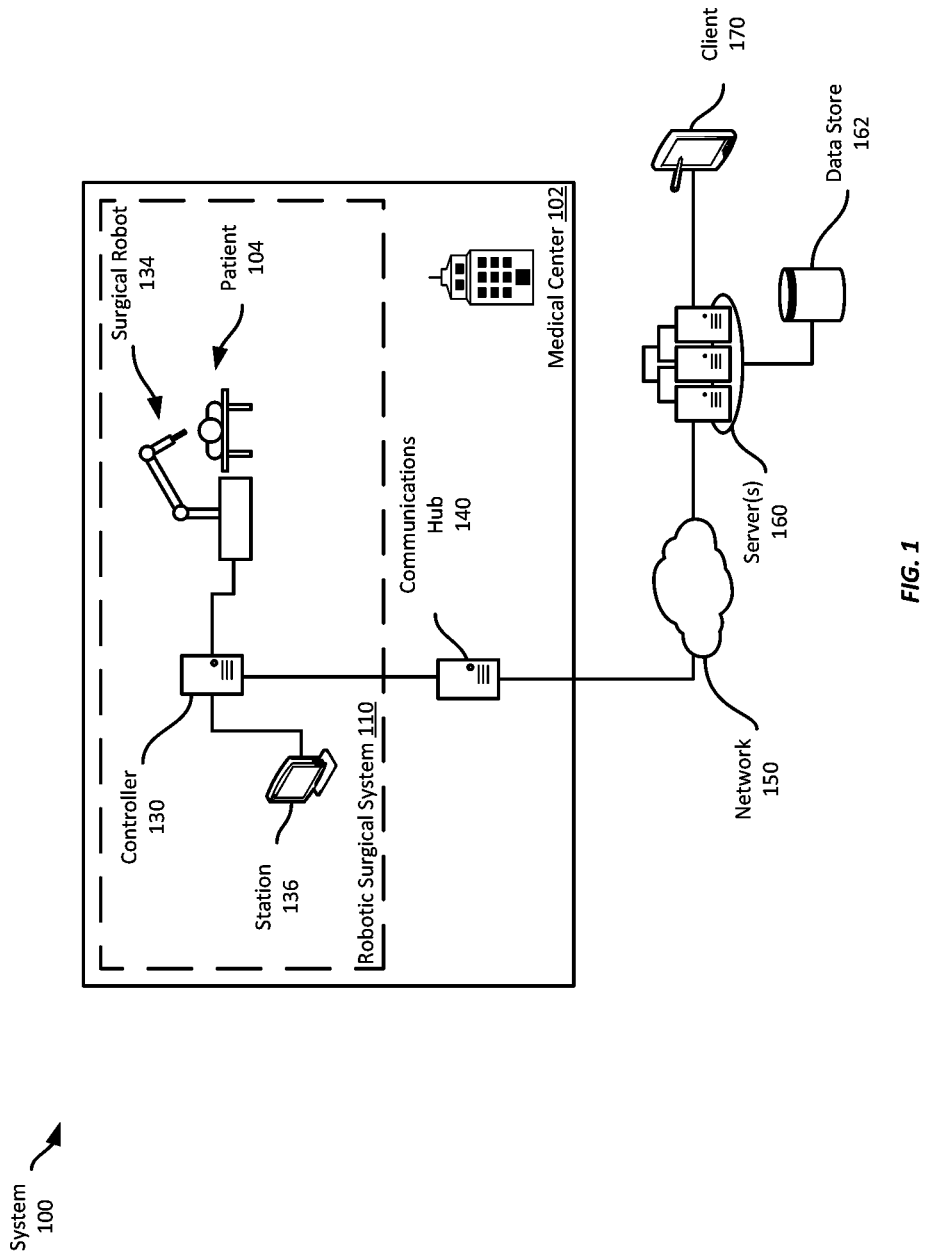
FIG. 1 shows an example system including a robotic surgical system for detecting delays during a surgical procedure.

Examples are described herein in the context of systems and methods for detecting delays during a surgical procedure. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In preparing for a robotic surgical procedure, a surgical robot will be configured with various tools used to perform the procedure, such as endoscopes, grasping tools, cutting tools, energy tools (e.g., cautery tools), etc. Because the surgery is performed, at least in part, using the robot, the surgeon controls the surgery by using input devices to control the tools connected to arms of the surgical robot, guided by a real-time view of the surgical site provided by a camera affixed to a tool, such as an endoscope.

Once the surgeon begins the surgery using the surgical robot, the video feed is provided on a display screen for the surgeon to view. The surgical robotic system also analyzes the incoming video feed to identify the type of surgical procedure, if not previously provided to the system, or the particular step of the surgical procedure the surgeon is performing, including potential detecting the specific action the surgeon is performing, e.g., cutting, stitching, cauterizing, etc.

Analysis of the incoming video is performed by one or more trained machine-learning ("ML") techniques that are provided excerpted frames from the video, e.g., at a lower frame rate than presented to the surgeon. The frames are presented to the ML technique(s), which generate probabilities (or scores) corresponding to different possible stages of the procedure and, in some cases, specific activities being performed during such stages. So long as the stage with the highest score exceeds a threshold, the ML technique supplies as output the identified stage (or activity) corresponding to that frame of video. A sequence of scores and corresponding frames generates a timeline of the procedure that the surgical robotic system maintains during the surgery (and potentially stores for long-term archiving, review, or further training of this or other ML techniques).

As the timeline is assembled, and the surgeon performs the surgery, the surgical robotic system access information regarding information about an expected time to complete ("TTC") the procedure as a whole, or to complete particular stages of the surgical procedure. For example, if a procedure is estimated to require three hours to complete and includes five stages, each stage having its own estimated time to complete, the robotic system can then attempt to predict an expected time remaining in the procedure. For example, when the robotic surgical system detects that the procedure has transitioned from stage two to stage three, it can use the estimated timing information for the procedure as a whole, and for stages three through five to determine how much more time the procedure is expected to take. In addition, the robotic surgical system can estimate a deviation from the typical time such a procedure is expected to take based on the predicted time remaining and the expected TTC at the present stage of the procedure. While slight deviations may be expected as each surgical procedure varies slightly from the others, once a deviation exceeds a threshold, it becomes highly likely that an unexpected event occurred leading to the increased or decreased expected TTC.

In addition to determining deviations from the expected TTC a particular procedure, the robotic surgical system can also estimate a time or event during the procedure that is the likely cause of the delay. For example, by using the accumulated timeline information and the baseline expected TTC information, the system can backtrack from the time at which the deviations is identified to a point when the calculated TTC and the expected TTC complete converge within a threshold amount. Video frames within a time range of that determined point may then be sent to a further ML technique to attempt to identify events or errors occurring near that point in the procedure.

For example, the ML techniques related to identifying stages of a surgical procedure, or activities within a surgical procedure, may not be trained to identify events such as excess adhesions or visceral fat deposits, unexpected bleeding, unexpected tool usage, or unplanned actions. Thus one or more additional ML techniques may be supplied with video frames to identify such events. In addition, the robotic surgical system may track tool usage during the procedure and it may determine whether an unexpected tool was attached to a robotic arm at or near the identified point in the video.

After determining the deviation from the expected TTC, the robotic surgical system can then provide notifications to one or more individuals to inform them of the likely delay. For example, if an additional surgeon is scheduled to join the procedure at a particular stage, the robotic surgical system may cause a pager message to be sent to the surgeon to both inform her of the delay, but also to provide a projected new time she will be needed in the operating room. Alternatively, the robotic surgical system can output a message on a display screen in the OR to alert the other medical personnel that the procedure is running longer than expected and that tools needed for the next stage of the procedure will not be needed until a new predicted transition time. In some cases, the robotic surgical system can notify an anesthetist regarding the expected completion time to enable them to schedule and timely begin the withdrawal of the patient from anesthesia. Similarly, messages may be sent to hospital administration to enable staff to notify a patient's family that a procedure is going to run longer than expected and potentially provide a reason for the delay, without needing to send a member of the surgical team out of the OR.

After the surgical procedure is completed, the robotic surgical system can then store the video taken during the procedure and create metadata annotations corresponding to the video with information about the progress of the procedure, such as bookmarks indicating transitions between stages of the surgical procedure as well as bookmarks indicating when the procedure appeared to deviate from the expected course of the procedure. The video and corresponding metadata can then be uploaded to a repository and a link provided to the surgeon (or others) to enable a post-hoc review of the procedure and any unexpected events. Similarly such video and the corresponding annotations may be employed to further train one or more ML techniques to further refine the accuracy of those techniques or to expand the range of issues that can be identified by such techniques.

A robotic surgical system equipped with such analytical capabilities can enable the system to provide real-time or near-real-time updates (e.g., within a few minutes of an event) regarding progress of a surgical procedure, unexpected events occurring during such a procedure, and delays in the completion of a particular activity, a stage of a surgical procedure, or the surgical procedure itself. Further, such techniques can be used to provide annotations to video recorded during the surgical procedure to enable expedited review of the issues occurring in the procedure, either after the fact or potentially during the procedure itself. For example, an attending surgeon could be notified of the delay and quickly jump to the appropriate location in the video where the expected delay originated to determine whether additional assistance or guidance may be needed. Further, while this example describes a real-time analysis of video, recorded video may also be analyzed only after-the-fact to quickly identify where a surgical procedure may have gone awry, even if no immediately obvious cause is identified by the surgical team.

This illustrative example is given to introduce the reader to the general subject matter discussed herein and the disclosure is not limited to this example. The following sections describe various additional non-limiting examples and examples of systems and methods for detecting delays during a surgical procedure.

Referring now to FIG. 1, FIG. 1 shows an example system 100 including a robotic surgical system 110 for detecting delays during a surgical procedure. The example system 100 includes the robotic surgical system 110 located at a medical center 102 that is in communication with one or more remote servers 160 via a communications network 150, such as the Internet. The remote server(s) 160 have an associated data store 162 than may include one or more databases or other servers. A user may use client 170 to access the server(s) 160, such as to create or edit surgeries to be performed, or to review videos obtained during a robotic surgical procedure.

The robotic surgical system 110 includes a controller 130, a surgical robot 134, and a station 136 usable by personnel in the OR, such as to view surgery information, video, etc., from the surgical robot 134, which may be used to operate on a patient 104 (though the patient is not part of the robotic surgical system 110). The controller 130 is in communication with an optional communications hub 140 that enables, optimizes, or improves communication to the remote server(s) 160 via the network 150. In addition, the communications hub 140 provides access to patient or other medical stored locally at the medical center 102. Further, in some examples the communications hub 140 may operate as a remote server 160, such as in one example in which the communications hub 140 is not local to the medical center 102.

The surgical robot 134 is any suitable robotic system that can be used to perform surgical procedures on a patient, to provide simulations of surgical procedures, or to provide training functionality to allow a surgeon to learn how to control a surgical robot 134, e.g., using exercises to train particular movements or general dexterity, precision, etc. It should be appreciated that discussions throughout this detailed description related to surgical procedures are equally applicable to simulated procedures or training exercises using a surgical robot 134. A surgical robot 134 may have one or more articulating arms connected to a base. The arms may be manipulated by a controller 130, which may include one or more user interface devices, such as joysticks, knobs, handles, or other rotatable or translatable devices to effect movement of one or more of the articulating arms, as well as one or more display devices to display information to the surgeon during surgery, e.g., video from an endoscope, information from patient medical records, previously obtained images (e.g., X-rays, MRI images, etc.). The articulating arms may be equipped with one or more surgical instruments to perform aspects of a surgical procedure. Different surgical robots 134 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without articulating arms, such as for endoscopy procedures, may be employed according to different examples.

In some examples, surgical robots (or a respective controller, e.g., controller 130) may be configured to record data during a surgical procedure. For example, the surgical robot 134 may record inputs made by the user, actions taken by the surgical robot 134, times (e.g., timestamps) associated with each input or action, video from one or more cameras of the surgical robot, etc. In some examples, surgical robot may include one or more sensors that can provide sensor signals, such as thermocouples, pulse sensors, SvO2 or SpO2 sensors, one or more cameras, etc., or other information to be recorded, such as temperatures, pulse information, images, video, etc. Such information may be obtained by the sensor and transmitted to a computing device within the surgical robot 134 itself or to the controller 130 for storage. Furthermore, while only one surgical robot 134 is depicted, any suitable number of surgical robots may be employed within a surgical robotic system 100.

The controller 130 in this example includes a computing device in communication with the surgical robot 134 and is able to control access and use of the robot. For example, the controller 130 may require that a user authenticate herself before allowing access to or control of the surgical robot 134. As mentioned above, the controller 130 may include, or have connected to it, one or more user input devices capable of providing input to the controller, such as a keyboard, mouse, or touchscreen, capable of controlling the surgical robot 134, such as one or more joysticks, knobs, handles, dials, pedals, etc.

To begin a surgery, a user may log into the controller 130, and the controller 130 may then activate the surgical robot 134, provide access to the surgical robot 134 to the surgery team, and provide access to patient information, including copies of one or more EHR records, patient images (e.g., x-rays, ultrasounds, etc.), etc.

As discussed above, the robotic surgical system 110 includes a communications hub 140 that includes a computer or server that manages communications with the controller 130 and surgical robot 134 within the medical center 102 and provides communications out of the medical center 102 and to the network 150. For example, the communications hub 140 may include a networking device, such as a router or a switch. However, the communications hub 140 may include one or more server devices that provide additional features, such as user access to patient or other medical records received from the server(s) 160, etc., while also providing secure access to locally stored medical records to the controller 130 or surgical robot 134. In some examples, the communications hub 140 is an optional component that may be omitted, or may be a virtual machine running on an underlying computing system.

It should be appreciated that while this example shows only one surgical robot 134 and controller 130 in communication with the communications hub 140, in some examples, the communications hub 140 may be in communication with multiple controllers 130 and surgical robots 134. For example, the medical center 102 may have one communications hub 140 per floor, or one for every four surgical robot 134/controller 130 combination, etc. In some examples, the medical center 102 may only have a single communications hub 140 that is in communication with all controllers 130 and surgical robots 134 at the medical center 102.

As discussed above, the robotic surgical system 110 is in communication with one or more remote servers 160 via network 150. The network 150 may be any combination of local area networks ("LAN"), wide area networks ("WAN"), e.g., the internet, etc. that enable electronic communications between the communications hub 140 and the remote servers 160.

The remote server(s) 160, in conjunction with the data store 162, store records about one or more surgeries to be performed, previously performed surgeries, videos from previously performed surgeries, to enable a user to create new surgeries, schedule the surgeries, assign medical personnel, assign a patient, allocate an OR and a robotic surgical system for the surgery, and review videos obtained during prior surgeries to prepare for an upcoming surgery or evaluate the performance of the previously performed surgery, etc. Thus, the server(s) 160 provides management and administrative control over the creation of new surgeries and the access to the data underlying those surgeries. It also provides a web portal that a user may access via a client 170 to create new surgeries, manage previously created surgeries, and access information regarding previously performed surgeries, such as videos and corresponding metadata.

During surgery, the surgical robot 134 captures video via one or more surgical tools, such as an endoscope, and transmits the video to the controller 130. The controller 130 outputs the video to one or more displays, such as a display at the controller 130 or another location, such as station 136. In addition, the controller 130 processes the incoming video in real-time or near-real-time using one or more trained ML techniques to detect the current phase of the surgery or activities being performed during the surgery. However, in some examples, the controller 130 may instead stream the video to a remote device to process the video in real-time or near-real-time, e.g., the controller 130 may stream the video to the communications hub 140 or to a remote computing device, e.g., remote server(s) 160, for processing. Alternatively, processing may not be done in real-time (or near-real-time), but may instead be processed after the surgery for analysis and review of the procedure, e.g., to help determine inefficiencies, errors, etc. that can be used to train one or more surgeons.

Figure 2:
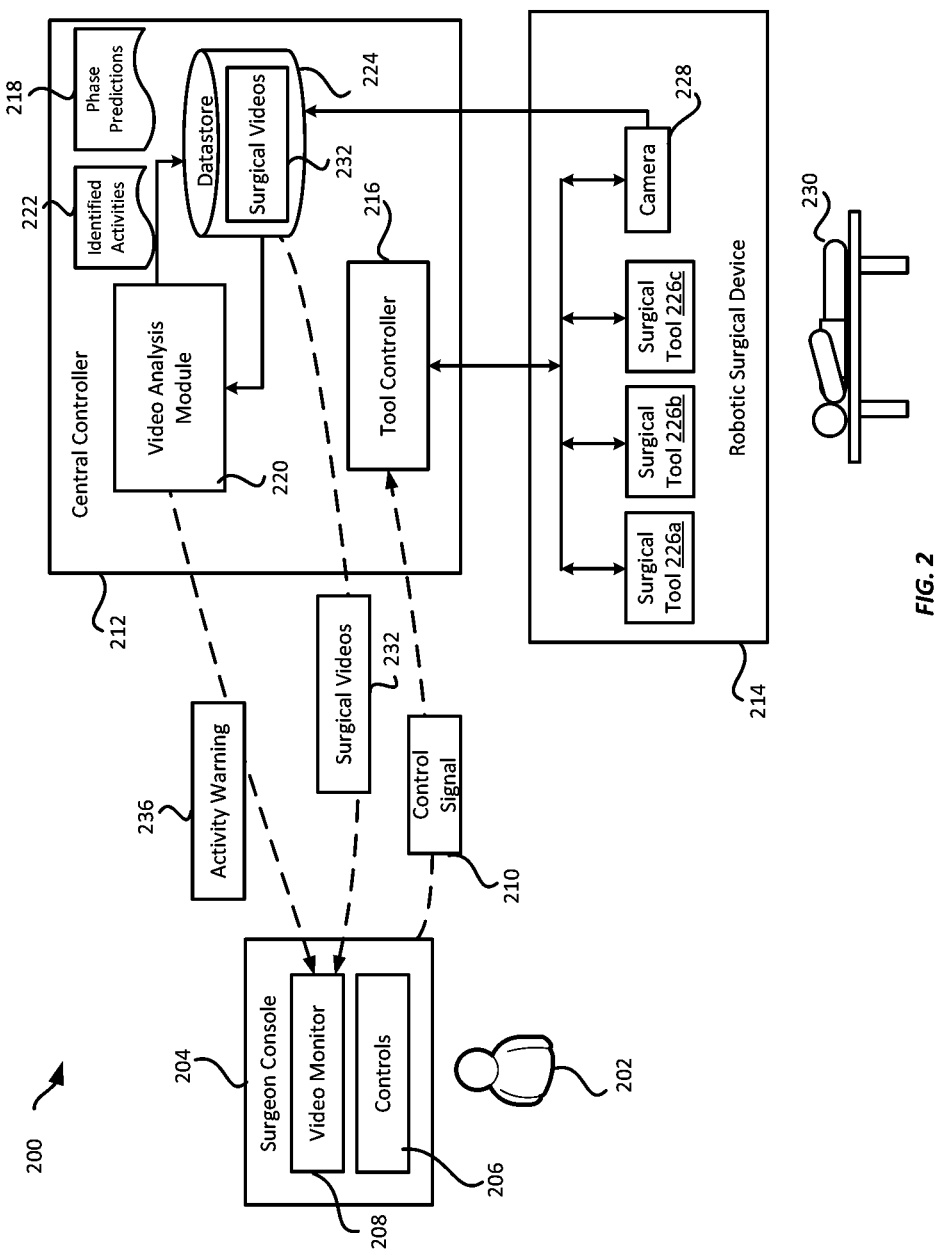
FIG. 2 shows an example system for detecting delays during a surgical procedure.

Referring now to FIG. 2, FIG. 2 shows an example system for detecting delays during a surgical procedure. This example robotic surgical system 200 includes a robotic surgical device 214 configured to operate on a patient 230, and a central controller 212 to control the robotic surgical device 214. The robotic surgical system 200 also includes a surgeon console 204 connected to the central controller 212 and the robotic surgical device 214. The surgeon console 204 is operated by a surgeon 202 to control and monitor the surgeries performed using the robotic surgical device 214. In addition to these components, the robotic surgical system 200 might include additional stations (such as station 136 shown in FIG. 1) that can be used by other personnel in the operating room, for example, to view surgery information, video, etc., sent from the robotic surgical device 214. In this example, the robotic surgical device 214, the central controller 212, the surgeon console 204 and other stations are connected directly to each other, though in some examples they may be connected using a network, such as a local-area network ("LAN"), a wide-area network ("WAN"), or any other networking topology known in the art that connects the various stations in the robotic surgical system 200.

The robotic surgical device 214 can be any suitable robotic system utilized to perform surgical procedures on a patient. For example, the robotic surgical device 214 may have one or more robotic arms connected to a base. The robotic arms may be manipulated by a tool controller 216, which may include one or more user interface devices, such as joysticks, knobs, handles, or other rotatable or translatable devices to effect movement of one or more of the robotic arms. The robotic arms may be equipped with one or more surgical tools to perform aspects of a surgical procedure. For example, the robotic arms may be equipped with surgical tools 226A-226C. Each of the surgical tools can be controlled by the surgeon 202 through the surgeon console 204 and the tool controller 216.

In addition, the robotic surgical device 214 is equipped with one or more cameras 228, such as an endoscope camera, configured to provide a view of the operating site to guide the surgeon 202 during the surgery. In some examples, the camera 228 can be attached to one of the robotic arms of the robotic surgical device 214 controlled by the tool controller 216 as shown in FIG. 2. In other examples, the camera 228 can be attached to a mechanical structure of the robotic surgical device 214 that is separate from the robotic arms, such as a dedicated arm for carrying the camera 228.

Different robotic surgical devices 214 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one robotic surgical device 214 is depicted, any suitable number of robotic surgical devices may be employed within a robotic surgical system 200.

In some examples, robotic surgical devices (or a respective controller) may be configured to record data during a surgical procedure. For example, images and videos of the surgical procedures performed by the robotic surgical device 214 can also be recorded and stored for further use. For instance, a storage server 224 can be employed by the robotic surgical device 214 to store surgical videos 232 of surgical procedures captured by the camera 228.

In the example shown in FIG. 2, surgical videos 232 of a robotic surgical procedure captured by the camera 228 can also be transmitted to the surgeon console 204 and be displayed on a video monitor 208 in real time so that the surgeon 202 can view the procedure while the surgical tools 226 are being used to operate on the patient 230. In this example, the surgeon 202 uses the surgeon console 204 to control the surgical tools 226 and the camera 228, and uses controls 206 on the surgeon console 204 to maneuver the surgical tools 226 and camera 228 by sending corresponding control signals 210 to the tool controller 216.

As shown in FIG. 2, the central controller 212 also includes a video analysis module 220 to process the surgical videos 232 captured during the surgery procedure. The video analysis module 220 analyzes the surgical videos 232 to predict workflow phases 218 of the ongoing surgical procedure or to identify various activities 222 occurring during the procedure. If the identified activities 222 include unusual events, such as bleeding, the central controller 212 may generate one or more activity warnings 236 which are presented on the video monitor 208 of the surgeon console 204 to notify the surgeon 202 about the unusual activity. The phase prediction 218 (also referred to herein as "predicted phase 218") and the identified activities 222 are stored in the storage server 224, in this example, along with the surgical videos 232 for future uses, such as archiving, indexing, post-surgery analysis, training of new surgeons, and so on.

It should be appreciated that although FIG. 2 illustrates the presented technique of surgical workflow phase and activity detection in the context of a robotic surgical system 200, it can be implemented in other types of systems and settings. For example, this technique can be implemented in a computing device separate from a robotic surgical system 200 and/or be performed offline after the surgical procedure is completed.

Figure 3:
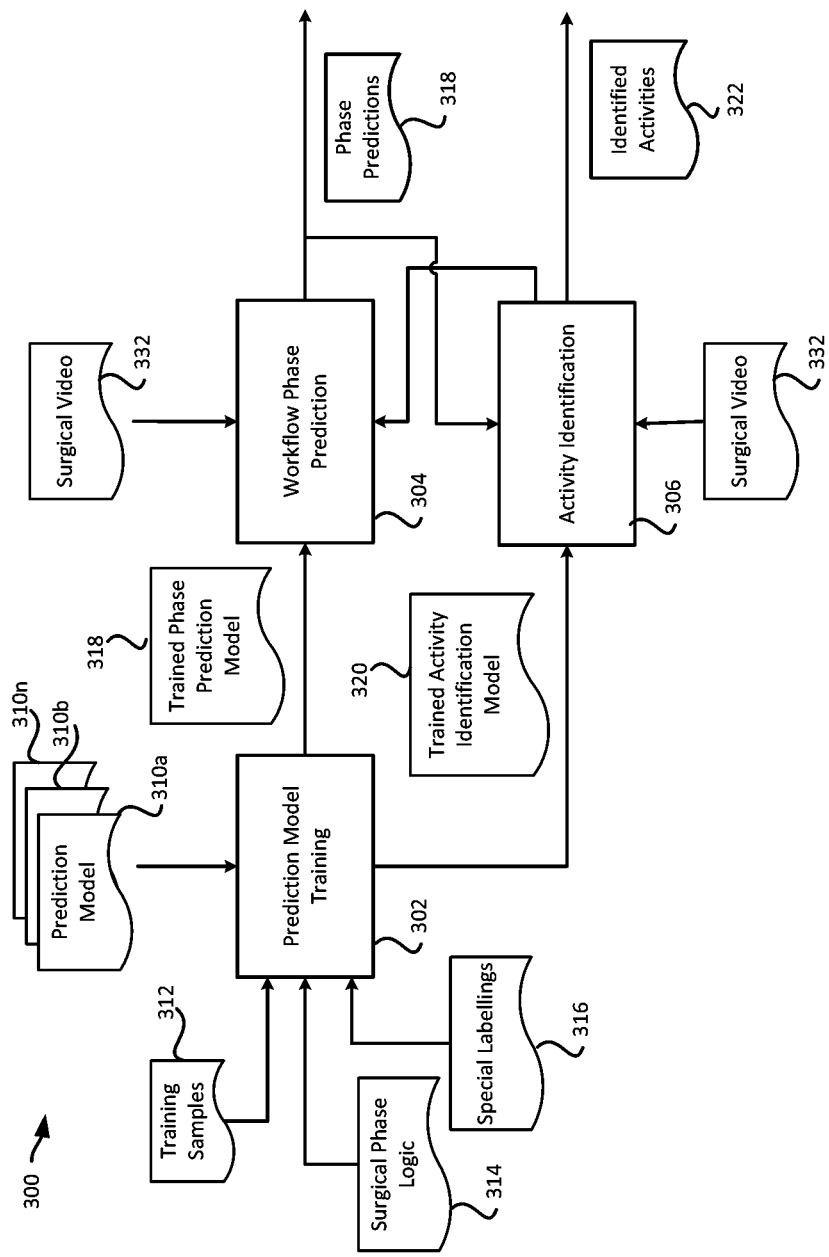
FIG. 3 shows a block diagram illustrating aspects of a video analysis system configured to detect surgical workflow phases and activities based on a surgical video.

Referring now to FIG. 3, FIG. 3 shows a block diagram illustrating aspects of a video analysis system 330 configured to detect surgical workflow phases and activities based on a surgical video 332. As shown in FIG. 3, the surgical workflow and activity detection performed by the video analysis module 320 in this example include several stages: a prediction model training stage 302, a workflow phase prediction stage 304 and an activity identification stage 306. The prediction model training stage 302 builds and trains one or more prediction models 310a-310n ('n' represents any natural number) to be used by the other two stages (which may be referred to herein individually as a prediction model 310 or collectively as the prediction models 310). For example, the prediction models 310 can include a model for predicting workflow phases for a specific surgery procedure, such as a cholecystectomy, a nephrectomy, a colectomy, etc. The prediction models 310 can also include a model for recognizing or identifying a specific activity from a surgical video 332, such as a surgical task like suturing, dissection, cauterizing, cutting, irrigation and suction, or an event of interest like bleeding, bile leaking, etc. Still other types of prediction models may be employed in other examples according to this disclosure.

A prediction model 306 can be a machine-learning ("ML") model, such as a convolutional neural network ("CNN"), e.g. an inception neural network, a residual neural network ("Resnet") or NASNET provided by GOOGLE LLC from MOUNTAIN VIEW, CALIFORNIA, or a recurrent neural network, e.g., long short-term memory ("LSTM") models or gated recurrent units ("GRUs") models. The prediction model 306 can also be any other suitable ML model may be trained to predict phases or activities for video frames, such as a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). The video analysis module 320 may employ the same type of prediction model or different types of prediction models for the surgical phase and activity detection.

To train the various prediction models 310 in this example, training samples 312 for each prediction model 310 are generated. The training samples 312 for a specific prediction model 310 can include input video frame(s) (or input features of video frames) and labels corresponding to the input video frames (or input features). For example, for a prediction model 310 to be utilized to identify a bleeding event based on an input video frame, the input can be the video frame itself or features extracted from the frame and the label can include a flag showing whether a bleeding has occurred in the input frame or not. Similarly, for a prediction model 310 to be utilized to predict a workflow phase for a video frame, the input can include the video frame or features extracted from the video frame, and the label can include a number indicating the phase the input video frame belongs to or a vector indicating probabilities the video frame belonging to different phases.

The training process includes iterative operations to find a set of parameters for the prediction model 310 that minimizes a loss function for the prediction models 310. Each iteration can involve finding a set of parameters for the prediction model 310 so that the value of the loss function using the set of parameters is smaller than the value of the loss function using another set of parameters in a previous iteration. The loss function can be constructed to measure the difference between the outputs predicted using the prediction models 310 and the labels contained in the training samples 312. Once the set of parameters are identified, the prediction model 310 has been trained and can be utilized for prediction as designed.

In addition to the training samples 312, other information can also be employed to refine the training process of the prediction models 310. For example, in a surgical video, some video frames are representative frames of the surgical procedure, such as frames containing representative actions or events during the surgical procedure. These video frames, once identified, can provide clues for the surgical phase of the video frames close to the representative frames. For instance, in cholecystectomy, dissecting can be performed either in the calot triangle area or between the gallbladder and the liver. Video frames showing activities in these areas can indicate that a dissecting phase of the cholecystectomy is occurring in the video. In another example, video frames showing the complete detachment of the gallbladder from the liver bed can be representative frames indicating the end of a surgical procedure. In yet another example, the presence of certain surgical tools can also be an indicator of the surgical workflow phases. For example, a stapler surgical tool detected from the video frames can indicate that the video frames describe a sleeve gastrectomy stomach stapling phase of the surgery.

These representative frames can be marked with additional labels indicating their representativeness. During the training of a phase prediction model 310, a higher weight can be assigned to a term of the loss function that corresponds to these representative frames. As a result, the trained prediction models 310 can give more weights to input frames that are similar to the representative frames when predicting the workflow phases.

In addition, surgical phase logic 314 can be incorporated into the prediction model training stage 302 to ensure that the phase predicted by a phase prediction model 310 does not violate the surgical phase logic 314. A surgical procedure generally has inherent logic among the different phases of the procedure. For example, gallbladder packaging can only happen after gallbladder dissection in cholecystectomy, and gastrojejunal anastomosis can only happen after dividing the jejunum in gastric bypass. The inherent logical relationship between the phases of a surgical procedure can be exploited to facilitate the phase prediction.

According to some aspects of the disclosure presented herein, the logical relationship between the workflow phases of a surgical procedure can be formulated as one or more constraints to the optimization problem discussed above for training the prediction models 310. A training loss function that penalizes the violation of the constraints can be built so that the training can take into account the workflow phase logic constraints. Alternatively, or additionally, structures, such as a directed graph, that describe the current features and the temporal dependencies of the prediction output can be used to adjust or refine the features and predictions of the prediction models 310. In an example implementation, features are extracted from a current video frame and combined with features from previous frames and later frames as indicated in the directed graph. Features generated in this way can inherently incorporate the temporal, and thus the logical, relationship between the frames in the training samples 312. Accordingly, the prediction models 310 trained using these features can capture the logical relationships between the various phases of the surgical workflow.

As discussed above, surgical videos are typically long and can last several hours or more. Obtaining the labels in the training samples 312 requires the expertise of medical professionals manually reviewing these videos, and is therefore a time consuming task. As a result, it is impractical for medical professionals to label all the surgical videos and thus a large number of surgical videos remain unlabeled. These unlabeled surgical videos, which may be cheaper to acquire than the labelled surgical videos, can also be employed to train the prediction models 310. For example, for an unlabeled training video, the prediction model 310 can be applied to predict its phase. If the predicted phase violates the inherent logic of the surgical procedure, this unlabeled video can be penalized by introducing a term in the loss function. That is, those unlabeled training videos whose predicted phase violates the inherent logic of the surgical procedure can be utilized to redefine the training loss function. As a result, the training loss function can be a combination of labelled video loss, as discussed above, and surgical step logic losses based on the unlabeled videos.

If, on the other hand, the predicted phase for an unlabeled training video using the prediction model 310 does not violate the inherent logic of the surgical procedure, the loss function can remain unchanged. As a result, the unlabeled training videos can have impact on the loss function only when the inherent logic of the surgical procedure is violated. By contrast, labeled videos can have impact on the loss function regardless of their violation of the inherent logic of the surgical procedure.

It should be understood that the above example is merely illustrative. The unlabeled videos can be utilized in various other ways during the prediction model training stage 302. For instance, the unlabeled videos can be utilized as training samples 312, for example, to include unsupervised losses such as smoothness of the prediction, as well as for enforcing the inherent logic of the surgical procedure. In this way, an unlabeled video can have a corresponding term in the loss function even if its predicted phase does not violate the inherent logic of the surgical procedure.

Similarly, auxiliary information can be utilized during the training of activity identification models 310. Preparing training samples 312 can involve manually labelling the input videos for the types of activities to be identified. It is challenging and laborious to label every single occurrence of surgical activities in the hour-long surgical videos. For example, a grasping action typically lasts a few seconds at once, but occurs multiple times in a surgical procedure. The training mechanism described herein allows a medical professional to label a manageable number of occurrences of these types of actions and mark the rest as "unknown." During training of the prediction models 310, the "unknown" labels are not used and excluded as part of the training loss function for these specific labels. This can prevent the unlabeled video frames from being treated as negative examples, e.g. target activities being identified as absent from the input video frames, though these "unknown" labels may later be determined by providing the video to a trained model for analysis. Alternatively, or additionally, selected sets of positive examples and negative examples can be generated and the model can be fine-tuned using these positive and negative examples.

In addition, the training mechanism described herein also allows hierarchical or multiple labeling. Surgical tasks and more fine-grained subtasks can overlap, and one task can contain multiple subtasks. As a result, multiple labels can be marked for the same video frame. For example, multiple anatomical structures and multiple surgical instruments can appear in the same video frame. As such, multiple surgical actions or tasks can happen concurrently in the same video, with possible accompanying events. By allowing multiple labels in a given frame, potential knowledge contained in a training video frame can be fully exploited by the video analysis module to train the activity identification models 310.

Although the training mechanisms described above mainly focus on training a prediction model 310. These training mechanisms can also be utilized to fine tune existing prediction models 310 trained from other datasets. For example, in some cases, a prediction model 310 might have been pre-trained using non-surgical video frames or images. In those cases, the prediction models 310 can be retrained using the training samples 312 containing surgical videos and other auxiliary information as discussed above.

The prediction model training stage 302 outputs trained prediction models 310 including the trained phase prediction models 318 and trained activity identification models 320. The trained phase prediction models 318 can be utilized in the workflow phase prediction stage 304 to generate phase predictions 188 for an input surgical video 332. The trained activity identification models 320 can be utilized to identify activities in a surgical video 332 to generate identified activities 322 in the activity identification stage 306.

The workflow phase prediction stage 304 and activity identification stage 306 can proceed independently in some examples with separate models. For example, the workflow phase prediction stage 304 can apply the trained phase prediction models 318 on a surgical video 332 to generate phase predictions 318 without identifying surgical activities. Similarly, the activity identification stage 306 can apply the trained activity identification models 320 to a surgical video 332 or a portion of the surgical video 332 to identify activities occurred in the input video without identifying the workflow phases.

Alternatively, the workflow phase prediction stage 304 and the activity identification stage 306 can be conducted sequentially with one stage using the outputs of the other as inputs. For instance, for a given surgical video 332, the video analysis module 320 can perform the workflow phase prediction stage 304 first to generate phase predictions for the frames in the surgical video 332. Then for a specific phase, the video analysis module 320 can enter into the activity identification stage 306 using the video frames that are predicted to be in that specific phase to identify activities 322 occurred during that phase. In another implementation, the video analysis module 320 can enter into the activity identification stage 306 first to generate the identified activities 322 for the surgical video 332 or a portion of the surgical video 332. The identified activities 322 can then be utilized during the workflow phase prediction stage 304 to facilitate the prediction of the phase for the surgical video 332.

Figure 4A:
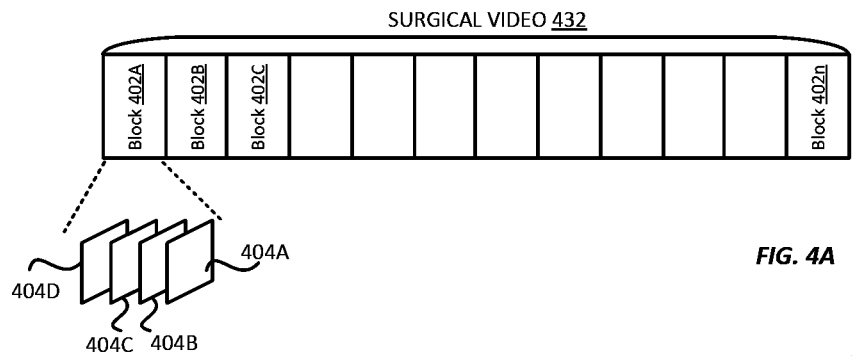
FIG. 4A illustrates a representation of a surgical video.
Figure 4B:
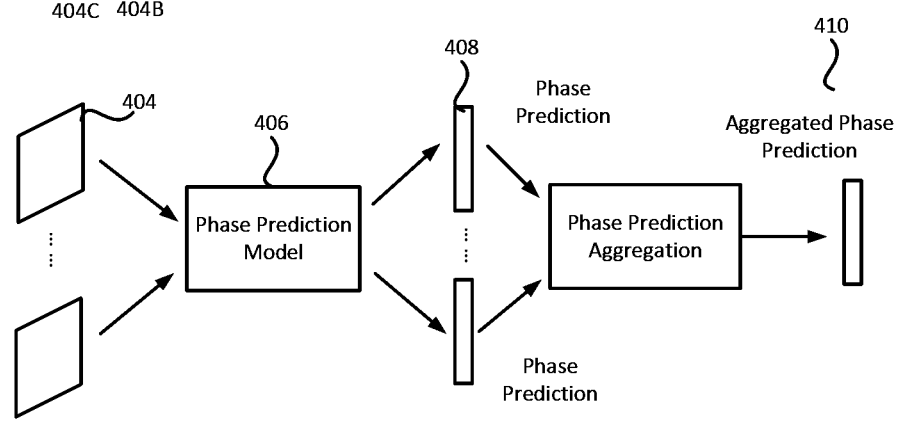
FIGS. 4B-4C illustrate examples of methods for predicting workflow phases for a video block.
Figure 4C:
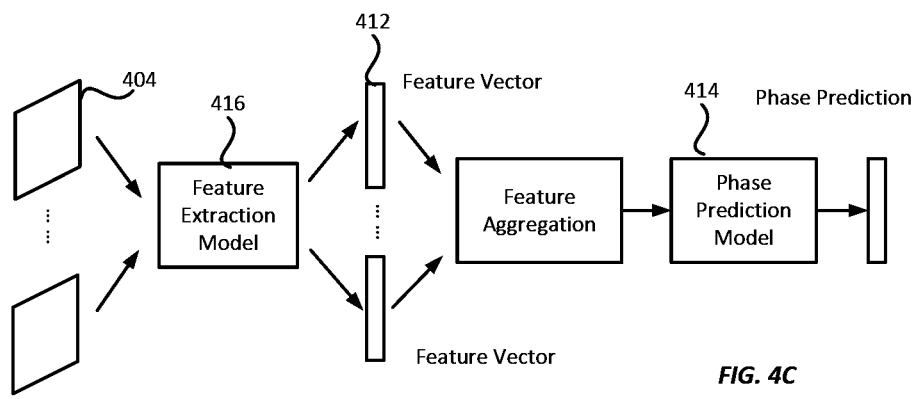

FIGS. 4A-4C show examples of methods for predicting workflow phases for a surgical video 432 in the workflow phase prediction stage 204. FIGS. 4A-4C will be presented in conjunction with FIG. 6A where a surgical video 432 with generated phase predictions is illustrated. FIG. 4A illustrates a surgical video 432. To generate phase predictions for the surgical video 432, the surgical video 432 can be divided into multiple video blocks 402A-402N (which may be referred to herein individually as a video block 402 or collectively as the video blocks 402). Each of the video blocks 402 can include multiple video frames or images 404A-404D (which may be referred to herein individually as a video frame or image 404 or collectively as the video frames or images 404). The size of the video blocks 402, e.g., the number of video frames 404 contained in a video block 402, can be the same or different for different video blocks 402.

FIG. 4B illustrates one example of a method for predicting workflow phases for a video block 402. In FIG. 4B, multiple video frames 404 can be extracted from a video block 402, such as by selecting one or two frames for every second of the video block 402. Each of the video frames 404 can be input into a phase prediction model 406, which may be a CNN, such as an inception neural network, a "Resnet" or NASNET.

The phase prediction model 406 can generate a phase prediction 408 for each of the video frames 404. The phase prediction 408 can include a single value indicating the workflow phase of the video frame 404 predicted by the phase prediction model 406. In some implementations, the phase prediction 408 can include a vector containing probabilities of different phases predicted for the input video frame 404. For example, the phase prediction 408 can include a vector p=[$p_1$, $p_2$, $p_3$, $p_4$] for a 4-phase surgical procedure, where $p_i$ represents the probability that the input video frame 404 is in phase i.

By feeding multiple video frames 404 into the phase prediction model 406, multiple phase predictions 408 can be generated. These phase predictions 408 can be utilized as the phase predictions for the respective frames. Alternatively, these phase prediction 408 can be aggregated to generate an aggregated phase prediction for the video block 402. The aggregation can help to reduce the impact of noises, such as prediction errors, on the phase prediction for the video block 402. In one implementation, the aggregation can be performed by temporally averaging the phase predictions 408 for the input video frames 404, that is:

$$p_{blk} = \frac{1}{M}\sum_{i=1}^{M} p_m \qquad (1)$$

where $p_m=[p_{m1}, p_{m2}, p_{m3}, \ldots p_{mT}]$ is the prediction vector for the $m^{th}$ input video frame 404 in a T-phase surgical procedure; M is the number of video frames that is fed into the phase prediction model 406; and $p_{blk}$ is the aggregated prediction vector for the video block 402.

The aggregated phase prediction 410 can then be analyzed to determine if a confidence level associated with the aggregated phase prediction 410 is high enough so that the prediction result can be trusted. In the above example, the prediction vector $p_{blk}$ contains probabilities of the input video block 402 belonging to respective workflow phases. The highest probability in the prediction vector $p_{blk}$ can be utilized to indicate the confidence level of the prediction. The workflow phase corresponding to the highest probability can be selected the predicted phase for the video block 402.

For example, three video frames 404 can be selected for a video block 402 and each can be fed into the phase prediction model 406 to generate three phase predictions 408 for a 4-phase surgical procedure: $p_1$=[0.1, 0.5, 0.2, 0.2], $p_2$=[0.1, 0.4, 0.3, 0.2] and $p_3$=[0.1, 0.8, 0.1, 0]. This means that the probabilities for a first video frame 404 belonging to the first to the fourth phase of the surgical procedure are 0.1, 0.5, 0.2 and 0.2, respectively. Similarly, the probabilities for a second video frame 404 belonging to the first to the fourth phase of the surgical procedure are 0.1, 0.4, 0.3 and 0.2, respectively, and the probabilities for a third video frame 404 belonging to the first to the fourth phase of the surgical procedure are 0.1, 0.8, 0.1 and 0, respectively.

Figure 6A:
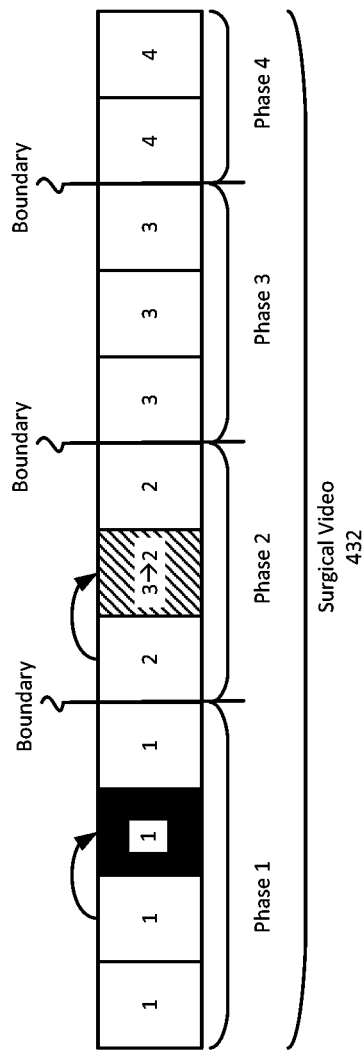
FIG. 6A shows an example surgical video with generated phase predictions generated for each of the video blocks.

The aggregated phase prediction 410 can be generated to be the average of the three phase predictions 408 as discussed above in Equation (1), i.e. $p_{blk}$=[0.1, 0.57, 0.2, 0.13]. In this case, the highest probability is 0.57 and the corresponding phase prediction for the current block is thus phase 2. Before selecting phase 2 as the final phase prediction for the current block, the highest probability 0.57 can be utilized as the confidence level of the phase prediction and be compared with a threshold value to determine if the phase prediction is reliable or not. If the threshold is set to be 0.55, then the phase prediction, i.e. phase 2 in the above example, can be selected as the phase prediction for the block. If, on the other hand, the threshold is set to be 0.7, the confidence level of the current phase prediction is not reliable enough and cannot be utilized as the phase prediction of the block. In the latter case, the phase prediction of a previous block can be utilized as the phase prediction for the current block. This is illustrated in FIG. 6A where the phase predictions generated for each of the video blocks 402 are shown. In this figure, the third video block of the surgical video 432 has a confidence level below the confidence threshold, and thus the aggregated phase prediction for that block is assigned to be the phase prediction of the second block.

It should be appreciated that the aggregation described above is for illustration only and should not be construed as limiting. Various other ways of aggregating the phase predictions for multiple frames of a video block can be utilized. For example, the phase predictions 408 can be aggregated by applying various linear or nonlinear functions. In scenarios where the phase prediction 408 include a single value indicating the predicted workflow phase for the frame, the aggregation of the phase predictions 408 can be performed by a majority voting among the multiple phase predictions 408.

Furthermore, the aggregated phase prediction 410 can be generated for each video frame 404, rather than each video block 402. For example, a sliding window of size M can be employed and applied to the phase predictions 408. For each frame video frame 404, its phase prediction 408 can be updated to be the average of the phase predictions 408 of its neighboring M frames as shown in Equation (1). As a result, the aggregated phase prediction 410 for a video frame 404 becomes a smoothed version of the phase prediction 408 using its neighboring video frames 404, thereby eliminating random noises in the phase prediction 408 and increasing its reliability. Similar to the aggregated phase prediction 410 for a video block 402, the confidence level of an aggregated phase prediction 410 for a frame is compared with a confidence threshold. If the confidence level is higher than the confidence threshold, the aggregated phase prediction 410 is utilized to determine the predicted phase for the video frame 404. If the confidence level is lower than the confidence threshold, the predicted phase for a previous video frame can be utilized as the predicted phase for the current video frame.

FIG. 4C illustrates an example of another overview of a method for predicting workflow phases for a video block 402. Similar to the method shown in FIG. 4B, multiple video frames 404 can be extracted from a video block 402, e.g. by selecting one or two frames for every second of the video block 402. Each of the selected video frame 404 can be analyzed to extract a feature vector 412. The feature vectors for the video frames 404 can then be aggregated to generate an aggregated feature vector, which is then sent to a phase prediction model 414 to generate the phase prediction for the video block 402.

The feature extraction for the video frames 404 can be performed in various ways. In some implementations, the feature vectors 412 can be extracted by applying a convolutional neural network on the video frame 404. For example, the feature vectors 412 can be generated as the phase prediction vectors by using the phase prediction model 406 in FIG. 4B. Similarly, the feature vectors 412 can be aggregated in a way similar to the phase prediction aggregation as described above regarding FIG. 4B. Alternatively, the aggregated feature vector can be aggregated by concatenating the feature vectors 412 to form a vector having a higher dimension than an individual feature vector. The aggregation of the feature vectors 412 can help to reduce the impact of noise in the feature extraction, as well as reducing the size of the input to the phase prediction model 414.

The phase prediction model 414 used in this example method can take the aggregated feature vector as input and output the phase prediction for the current block along with the confidence level. Considering the sequential nature of the workflow phases of a surgical procedure, a recurrent neural network can be utilized as the phase prediction model 414, such as LSTM models or GRUs models. In a recurrent neural network, connections between nodes form a directed graph along a sequence, which allows the neural network to exhibit temporal dynamic behavior for a time sequence. Similar to the example shown in FIG. 4B, the phase prediction generated by the phase prediction model 414 can include a vector of probabilities indicating the probabilities of the current block belonging to the respective phases. The phase prediction can also be associated with a confidence level, such as the highest probability in the probability vector. The confidence level can then be compared with the confidence threshold to determine whether the phase prediction generated by the phase prediction model 414 or the phase prediction of the previous block should be used for the current block as discussed above with respect to FIG. 4B.

The phase prediction method discussed above in FIG. 4B or FIG. 4C can be applied to each of the video blocks 402 of the surgical video 432. The output of the workflow phase prediction stage 204 is illustrated in FIG. 6A, where each video block 402 of the surgical video 432 can be predicted to be associated with one of the workflow phases of the surgical procedure.

In addition to the methods described above, other information can be utilized to refine or correct the phase prediction for a video block 402. For example, information such as changes of surgical tools may be logged and used to indicate a new surgical phase. In another example, as discussed above, a surgical procedure has an inherent logical relationship among the various workflow phases. For instance, gallbladder packaging can only happen after gallbladder dissection in cholecystectomy. In other words, a video block 402 cannot have a phase prediction that is later than the phase prediction of a subsequent video block 402. FIG. 6A illustrates an example of the scenario. In FIG. 6A, the $5^{th}$ video block of the surgical video 432 is predicted to be in phase 4, but the following block, i.e. the $6^{th}$ video block, is predicted to be in phase 2. As such, the phase prediction of the $5^{th}$ video block violates the inherent logic of the surgical procedure. To correct the inconsistency in the phase prediction, the phase prediction of a previous video block 402, i.e. $4^{th}$ video block in this example, can be utilized to replace the prediction of the current block. Similarly, if a video block 402 is predicted to be in a phase prior to the phase of its previous video block 402, the phase prediction of the current video block 402 can be replaced with the phase prediction of its previous video block 402. It should be understood that this example is for illustration only and should not construed as limiting. Various other ways of utilizing the inherent logic of the surgical procedure can be employed to modify the phase prediction.

Figure 4D:
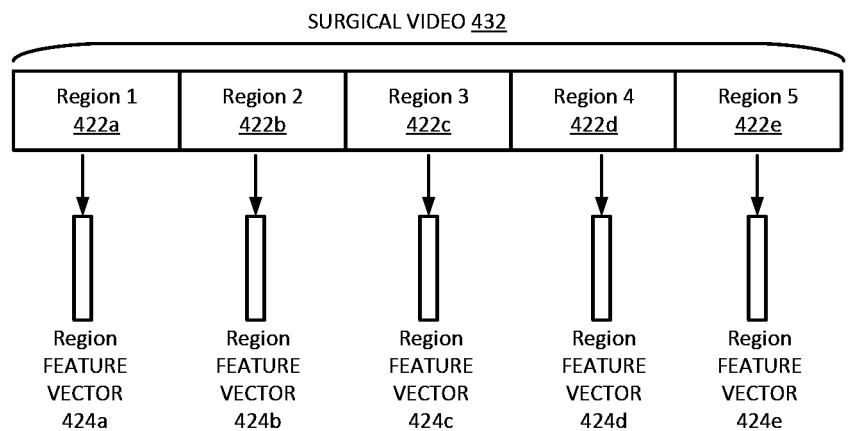
FIGS. 4D and 4E show an example of a method for improving the phase prediction of the surgical video.
Figure 4E:
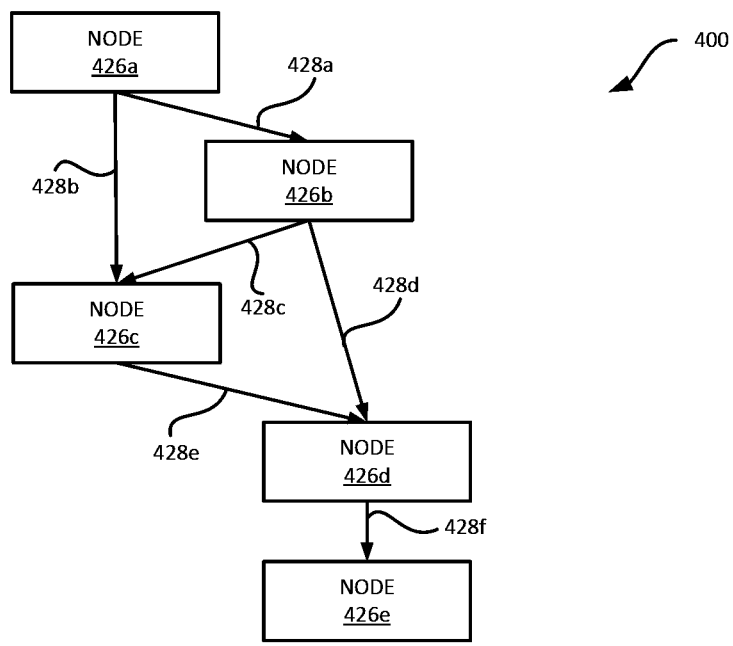

The phase prediction for the video can be further refined or improved by using the inherent logic of the workflow. FIGS. 4D and 4E show an example of a method for improving the phase prediction of the surgical video. In the example shown in FIG. 4D, the video analysis module 120 divides the surgical video 432 into multiple regions 422A-422E, which may be referred to herein individually as a region 422 or collectively as the regions 422. In one example, one region includes frames or video blocks that are predicted to be in the same phase. For example, video frames predicted to be in phase 1, as shown in FIG. 6A, can be included in region 1 422A; video frames predicted to be in phase 2 can be included in region 2 422B, and so on.

Region feature vectors 424A-424E (which may be referred to herein individually as a region feature vector 424 or collectively as the region feature vectors 424) are generated for the respective regions 422. In one example, the video analysis module 120 generates the region feature vector 424 by combining the phase predictions 408 of the frames, as shown in FIG. 4B, in the corresponding region 422 or by combining the feature vectors 412 of the frames, as shown in FIG. 4C, in the corresponding region 422. The combination can be performed by averaging the feature vectors 412 or the phase predictions 408 of the frames in a region 422. Alternatively, the combination can be performed by utilizing a machine learning model, such as a LSTM that is configured to accept a sequence of feature vectors 412 or phase predictions 408 and output a region feature vector 424.

It should be understood that the method of generating region feature vectors 424 described above is for illustration only and should not be construed as limiting. Various ways can be employed to generate the region feature vectors 424, For example, features other than the feature vectors 412 or phase predictions 408 can be extracted from the frames of a region 422, and these features can be combined to generate the region feature vector 424 using various linear and non-linear functions.

Based on the regions 422, the video analysis module 120 builds a directed graph to model the temporal relationship between the regions 422. The video analysis module 120 builds the directed graph based on various rules, such as rules reflecting the logical relationship among the phases of the workflow. An example of a directed graph 400 is shown in FIG. 4E. The directed graph 400 includes multiple nodes 426a-426e representing the regions 422a-422e shown in FIG. 4D, respectively. The arrows 428a-428f of the directed graph 400 indicate the temporal relationship among the nodes 426 and thus the regions 422. For example, the arrow 428a indicates that node 426b follows node 426a and the arrow 428d indicates that node 426d follows node 426b. The temporal relationship identified by the directed graph 400 also indicates the neighboring relationship among the nodes 426 and therefore the regions 422. For example, based on the directed graph 400, it can be determined that node 426c has three neighbors: node 426a, node 426b and node 426d, and thus the region 422c has three neighbors: region 422a, region 422b and region 422d.

Based on the neighboring relationship, the video analysis module 120 refines the phase prediction for the surgical video 432. In one example, the video analysis module 120 updates a region feature vector 424 associated with a region 422 by combining the region feature vector 424 of the region 422 with the region feature vectors 424 of its neighboring regions. In the above example, the region feature vector 424c is updated by combining it with the region feature vectors 424a, 424bn and 424d. Denote the region feature vector of the current region as $f_c$ and the region feature vectors of its neighboring regions as $f_{n1}, f_{n2}, \ldots, f_{nN}$, where N is the number of neighboring regions of the current region. The updated region feature vector of the current regions, $f'_c$, can formulated as:

$$f'_c = g(f_c, f_{n1}, f_{n2}, \ldots, f_{nN}) \quad (2)$$

where g( ) is a combination function used to combine these region feature vectors. In one implementation, the g( ) represents a weighted summation of these region feature vectors and a weight assigned to $f_c$ is higher than that of $f_{n1}$, $f_{n2}, \ldots, f_{nN}$. In other implementations, the combination function g( ) can be a machine learning model configured to accept multiple region feature vectors as inputs and output a combined regions feature vector, such as a graph neural network.

In further implementations, the updated region feature vectors can be updated again using the updated region feature vectors based on the directed graph 400 as described above. That is, $$f''_c = g(f'_c, f'_{n1}, f'_{n2}, \ldots, f'_{nN}) \quad (3)$$

In this way, the updated region feature vector can be impacted by its immediate neighbors, as well as the neighbors of the immediate neighbors. The updated region feature vectors are then sent to a machine learning model configured to predict the phase for an input region feature vector. In one example, the machine learning model is a fully-connected neural network where the input layer of the network has a dimension that is the same as the dimension of the updated region feature vector, and the output layer having a dimension equal to the number of the phases of the workflow. For a given input feature vector, the fully-connected neural network can predict one of the output phases as the corresponding phase for the input. Other types of machine learning models can also be utilized to predict the phase given the updated region feature vectors, such as a machine learning model similar to the phase prediction model 406 or the phase prediction model 414.

Another refinement on the phase prediction of the surgical video 432 involves boundary refinement of the predicted phases. In some implementations, such as the block-based method described above with respect to FIG. 4A-4C, the boundary of a predicted phase might deviate from the actual boundary of the phase due to the use of a video block as a unit for phase prediction. In other words, a video block may contain video frames from two adjacent phases, and the actual boundary of the phase might be in the middle of the block, rather than the border of the block. To correct the predicted phase boundary, the video analysis module 120 combines the feature vectors of two adjacent phases and feed the combined feature into a machine learning model configured to predict the boundary between the two adjacent phases.

For example, the video analysis module 120 can use the region feature vectors of the regions discussed above with respect to FIG. 4D as the features of the phases or use the feature vectors of the frames in the adjacent regions as discussed above regarding FIG. 4B. The combination of the region feature vectors of two adjacent phases can be performed by applying a recursive neural network as such a LSTM on the region feature vectors or on the frame feature vectors, or by applying a one-dimension convolutional neural network on these feature vectors. The combined feature vector is then input to a machine learning model trained to predict the boundary of the two adjacent phases. The machine learning model can be a neural network, such as a fully-connected neural network, or any other type of properly training machine learning model.

Figure 5:
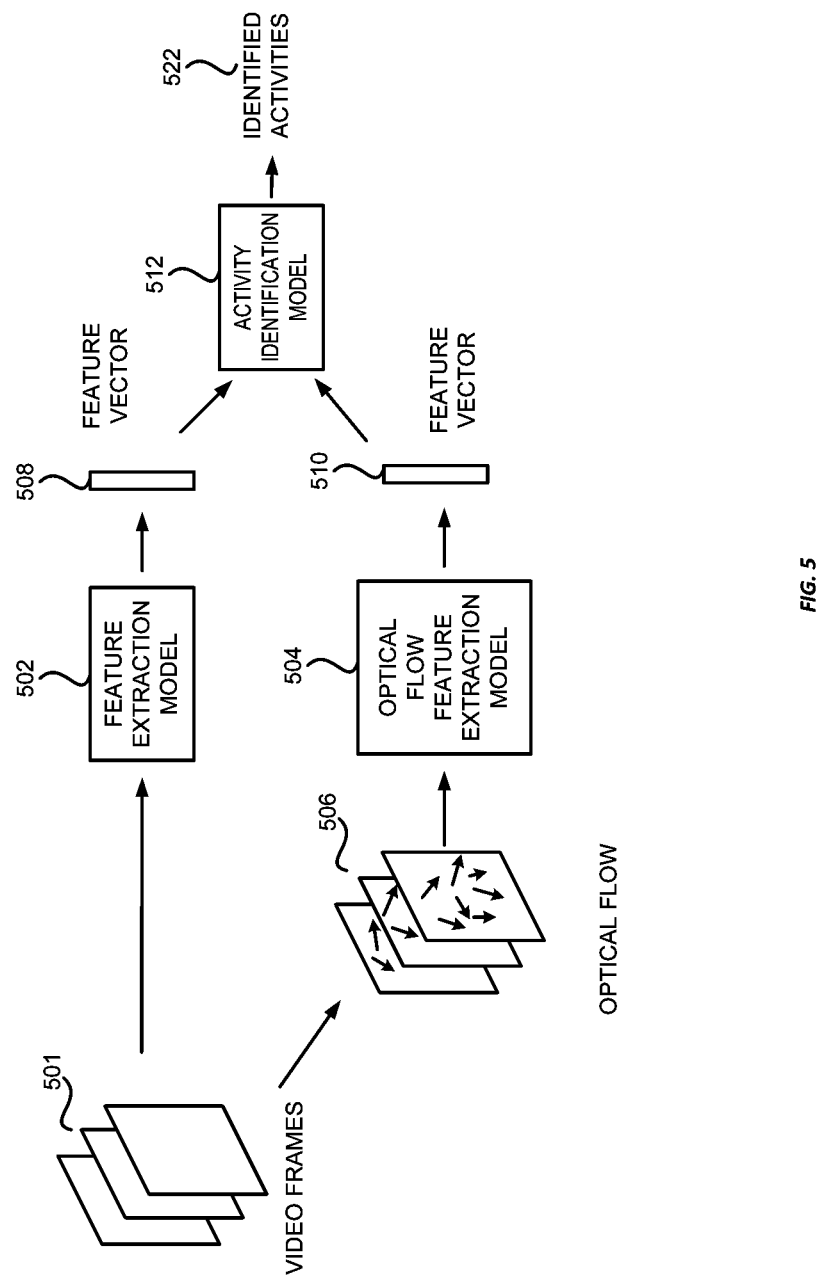
FIG. 5 shows an example of a method for identifying surgical activities, such as surgical tasks or events, from a surgical video.

Referring now to FIG. 5, FIG. 5 shows an example of a method for identifying surgical activities, such as surgical tasks or events, from a surgical video 432 in the activity identification stage 306. FIG. 5 will be discussed in conjunction with FIG. 5B where an example of an output of the activity identification stage 206 is illustrated. In the example shown in FIG. 5, a group of video frames 501 that are extracted from a video block 402 can be utilized to extract a feature vector 508 by a feature extraction model 502. In one implementation, the feature extraction model 502 can include a 3D convolutional neural network ("3DCNN") trained to generate feature vectors based on a group of input video frames. In addition, optical flows 506 can be extracted from the group of video frames 504. An optical flow is the pattern of apparent motion of objects, surfaces, and edges in the video frames 501. The optical flows 506 can be extracted from the video frames 501 using any optical flow extraction method known in the art. The extracted optical flows 506 are fed into an optical flow feature extraction model 504 to generate a feature vector 510. Similarly, the optical flow feature extraction model 504 can also include a 3DCNN trained to generate feature vectors based on optical flow inputs.

In some implementations, the feature vectors 508 and 510 can each include a probability vector containing probabilities of the group of video frames 501 having different activities. For example, a feature vector 508 or 510 can include a vector $q=[q_1, q_2, q_3, q_4, q_5, q_6]$, where $q_i$ represents the probability of the group of video frames 501 containing an activity i. The feature vectors 508 and 510 can then be combined and be utilized by an activity identification model 512 that is trained during the prediction model training stage 302 to generate the identified activities. The combination of the feature vectors 508 and 510 can include, but is not limited to, averaging of the two feature vectors, concatenating the two feature vectors, selecting a larger value of the two values for each vector element, or selecting a smaller value of the two values for each vector element. The activity identification model 512 can include a neural network model, such as a recurrent neural network, trained to identify surgical activities based on feature vectors generated from video frames and optical flows.

It should be understood that while FIG. 5 shows that an activity identification model 512 is utilized to output the identified activities, the identified activities can be generated by combining the feature vectors 508 and 510 without using the activity identification model 512. The combined feature vector can be compared with a threshold value and the activities corresponding to the probabilities that are higher than the threshold can be output as the identified activities.

It should be further appreciated that while the example method shown in FIG. 5 utilizes a feature extraction model 502 and an optical flow feature extraction model 504, the video analysis module 120 can utilize other types of models and methods in the activity identification stage 306. For example, a prediction model similar to the phase prediction model 406 can be employed to identify activities on a frame-by-frame basis similar to the methods shown in FIGS. 4B and 4C.

Based on the events or tasks detected during the surgical procedure, alerts can be generated and be presented to the surgeon 102 to notify him or her about the detected events or tasks. For example, if the prediction models used in the activity identification stage 306 is trained to identify bleeding events, similar bleeding events can be identified from a surgical video 432 captured during a surgical procedure. A warning message or other type of feedback can be provided by the video analysis module 120 to notify the surgeon 102 about the occurrence of the bleeding. Likewise, if the prediction models are further trained to identify different types of bleeding, such as a minor bleeding versus a major bleeding, the video analysis module 120 can identify these different types of bleeding and notify the surgeon 102 accordingly.

Figure 6B:
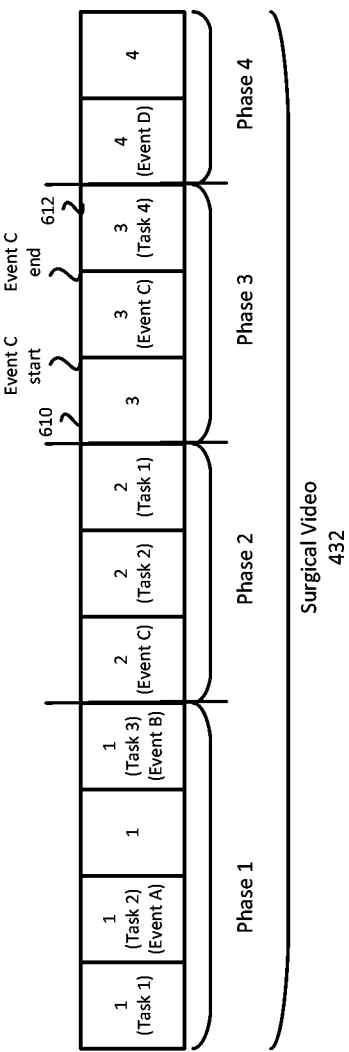
FIG. 6B shows an example output of the workflow phase prediction stage and the activity identification stage.

FIG. 6B shows an example output of the workflow phase prediction stage 304 and the activity identification stage 306. As shown in FIG. 6B, in addition to the phase prediction for each block 402, the identified activities, including surgical tasks and events, can also be utilized to annotate the corresponding portions of the surgical videos 432. The identified activities can also be further refined with respect to the start and end points of the respective activities. In one example, the video analysis module 120 performs the refinement of an identified activity by taking into account the neighboring video frames of the activity. For example, the start and end points of event C in phase 3 shown in FIG. 6B can be refined by considering the video frames before and after the event C, such as the video frames in the previous block 610 and the subsequent block 612. It should be understood that the neighboring frames can be selected by various ways other than based on the video blocks, such as by selecting a predetermined number of frames before and after the activities regardless of the video blocks.

Similar to the boundary refinement for detected workflow phases discussed above, the video analysis module combines the feature vectors of the frames containing the detected activity and the neighboring frames by applying a recursive neural network as such a LSTM or a one-dimension convolutional neural network to generate a combined feature vector. The combined feature vector is then fed into a machine learning model configured to predict the start and end points of the activity, such as a fully-connected neural network or any other type of properly training machine learning model, to predict the start and end points of the detected activity. Similar process can be applied to other detected activities to refine the start and end points of the respective activities.

As can be seen from FIG. 5B and the above discussion, the surgical workflow phase prediction and activity identification presented herein can automatically annotate a long surgical video so that the video can be indexed and archived for various purposes such as post-surgery analysis, educating new surgeons or for safety check. The annotation can be performed by generating and attaching metadata indicating the phases and activities to the surgical video. Alternatively, or additionally, the annotation can be performed by modifying the content of the video to mark the detected phases and activities, such as by inserting texts, images, icons or logos indicating the phases and activities into the video frames.

It should be understood that while FIG. 6B illustrates the results of both the phase prediction and activity identification, it is not necessary to perform both analyses for a given surgical video 432. In other words, for a surgical video 432, phase prediction can be performed without activity identification. Similarly, a portion of a surgical videos 432 can be utilized to identify activities without performing phase prediction on the portion of the surgical video 432.

Figure 7:
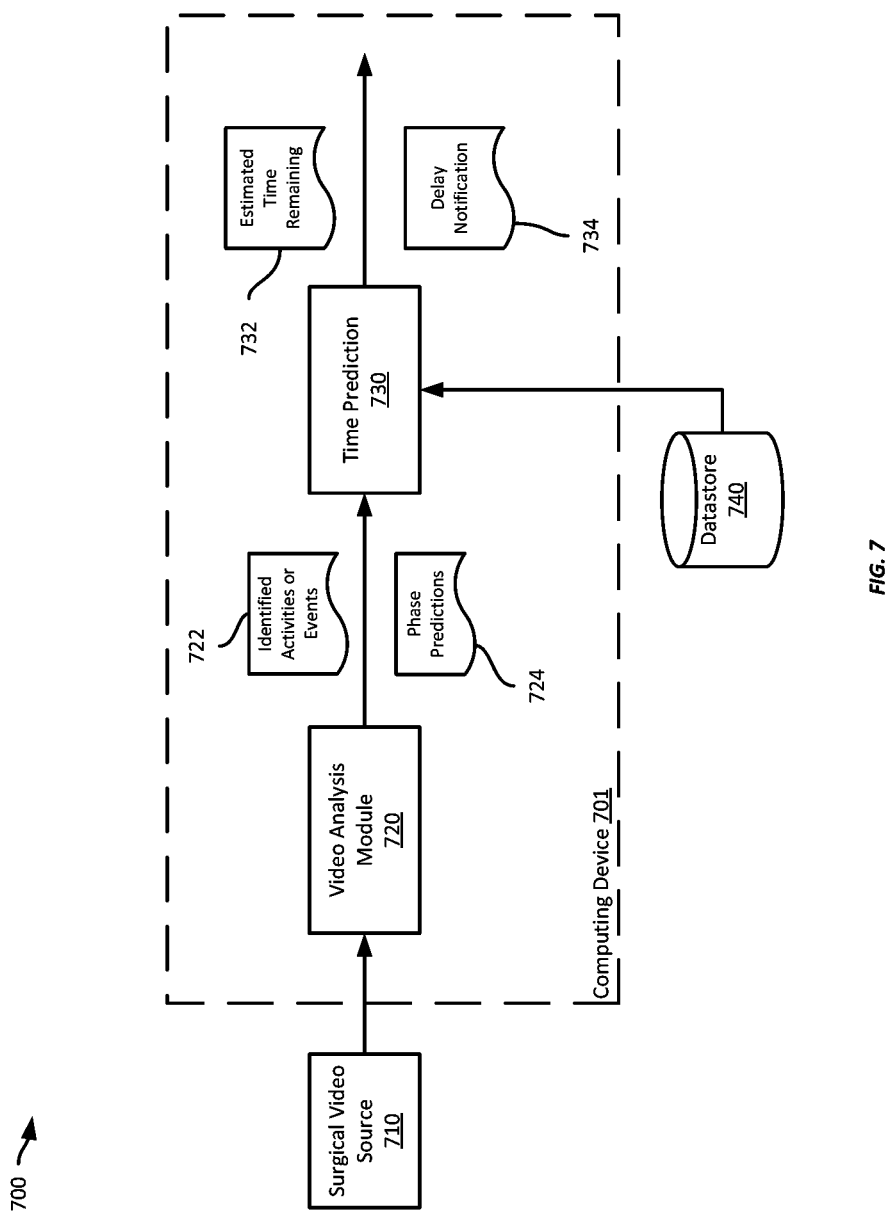
FIG. 7 shows an example system 700 for detecting delays during a surgical procedure.

Referring now to FIG. 7, FIG. 7 shows an example system 700 for detecting delays during a surgical procedure. In this example, the system 700 includes a computing device 701, a surgical video source 710, and a datastore 740. The surgical video source 710 is an endoscope camera connected to a robotic arm of a surgical robotic system, such as the robotic surgical device 214 shown in FIG. 2. The endoscope camera provides real-time streaming video to the system 700, which the computing device 701 processes as discussed below. However, in some examples, the surgical video source 710 may be a camera positioned within an operating room external to the patient, such as on a surgical robot, a robotic arm of a surgical robot, on a camera mount positioned near the patient, or elsewhere within the operating room. Further, in some examples the surgical video source 701 may be one or more datastores having previously recorded surgical videos, such as the data store 162 shown in FIG. 1 accessible via one or more remote servers 160, such as via a web portal. Thus, different example systems according to this disclosure may receive real-time video or may receive previously recorded video.

The computing device 701 is any suitable computing device that has been configured to detect delays during a surgical procedure. In this example, the computing device 701 includes a video analysis module 720 and a time prediction module 730. The video analysis module 720 may include any of the activity or phase prediction functionality discussed above with respect to FIG. 2, 3, 4A-4E, 5, or 6A-6B, or any equivalents. As shown in FIG. 7, the video analysis module 720 outputs identified activities or events 722 or phase predictions 724. The time prediction module 730 employs these outputs to predict a remaining time in a surgical procedure or to detect delays during the surgical procedure. In this example, the video analysis module 720 is in communication with the time prediction module 730, e.g., as part of the same software application, using inter-process communication, or by accessing a shared memory area. And while this example system 700 employs two discrete modules 720, 730, other examples may incorporate such functionality into a single module or may use more than two modules to provide such functionality. Further, some examples, may distribute such functionality across two or more computing devices.

In this example, the time prediction module 730 receives the identified activities or phase predictions, as discussed above, and also obtains information about the surgical procedure, such as from the datastore 740. For example, the datastore 740 may have data indicating the expected length of one or more surgical procedures, expected lengths of different phases of such surgical procedures, activities to be performed during such surgical procedures (or phases of such surgical procedures), etc. For example, the datastore 740 may include one or more lookup tables comprising such information.

The information about the surgical procedure may be provided as individual values corresponding to different surgical procedures or phases of different surgical procedures. For example, the datastore may include one or more records corresponding to a gastric bypass procedure. The record(s) may indicate an expected time to complete a gastric bypass procedure of 162 minutes. Further, the record (s) may identify one or more phases of the gastric bypass procedure and have associated durations for each phase. Thus, the time prediction module 730 may obtain these expected times to complete from the datastore 740. In some examples, the information about the surgical procedure may include statistical information, such as a mean duration for the surgical procedure and a standard deviation value (or other statistical information such as median, a full distribution curve, etc.), and similar such information for one or more phases of the surgical procedure.

Similarly, and as alluded to above, the information about the surgical procedure may include activities to be performed during the surgical procedure. Further such activities may have associated times during the surgery when they are expected to be performed, e.g., specific phases or at an expected elapsed time (or time window) during the surgical procedure or within a specific phase of the surgical procedure.

In addition to storing information about expected durations, phases, and activities, the datastore 740 may also maintain information about issues that may occur during a particular type of surgical procedure or conditions that may affect the course of the surgical procedure that may be used to scale or otherwise modify an expected duration of a surgical procedure or phase of a surgical procedure. For example, a patient's weight may impact the time required to perform a gastric bypass. Further, as the weight increases, it may not only impact the duration of one or more phases of the surgery, but it may implicate activities that are not otherwise employed during a gastric bypass. Thus, the datastore 740 may maintain one or more records identifying such conditions or events and information characterizing the impact on the duration of one or more phases of the surgical procedure, the duration of the surgical procedure itself, or the activities to be employed during the surgical procedure. Such information may be used to determine an expected duration before the surgery begins or, if one of the identified issues is detected by the system 700 during the surgical procedure, information stored in the datastore 740 associated with the identified issue may be used to both indicate the surgical procedure will take longer than originally expected and may be used adjust the expected time to completion of the surgical procedure.

Thus, the datastore 740 may store many different types of information that may be used to predict the expected time to complete a particular surgical procedure and, during the course of the surgical procedure, the estimated time remaining. As discussed above, such information may include timing information or sequence information about the expected course of a surgical procedure, including phases (sequence or duration), expected activities (sequence or duration), common events or activities, known issues or conditions and their impact on the course of the surgical procedure, etc.

Referring again to the time prediction module 730, the time prediction module receives phase predictions, identified activities, and information about the surgical procedure and determines an estimated time remaining in the surgical procedure. It then provides one or more of an estimated time remaining in the surgical procedure, an estimated time remaining in the then-current phase of the surgical procedure, or one or more delay notifications.

By providing an estimated time remaining in the surgical procedure, hospital staff can more precisely schedule or notify staff of an upcoming procedure's anticipated start time, which may enable the staff to more efficiently prepare for the upcoming procedure, such as by prepping the patient, prepping tools or supplies for the procedure, alerting personnel, e.g., by sending a pager message, text message, or email, about when they will be needed, etc. More granular information about estimated time to complete a particular phase of a surgical procedure may be displayed within the OR and used by medical personnel to timely prep tools, supplies, notify an attending or other senior surgeon to check in on the surgery, etc. for the next phase of the procedure, notify a surgeon to report to the OR for a particular phase of the procedure, etc. Further, as the estimated times change or if delays are determined by the system 700, whether for the entire surgical procedure or for a particular phase, medical personnel may be notified of the delays to help prevent staff from arriving too early, notify hospital staff that a subsequent surgery will be delayed, notify the patient's family about the delay, etc.

In addition to predicting the remaining time, the system 700 may also determine a likely cause of a delay. For example, the time prediction module 700 during a surgical procedure may maintain a history of predicted times to complete the surgical procedure and track the changes over time to the predicted time to complete. If the surgery is progressing normally, the expected time to complete should decrease by approximately one minute for every elapsed minute of surgery, e.g., the slope of a curve mapping expected time (the "expected curve") to complete and elapsed time should be approximately 1 or the area between the expected curve and a reference line having a slope of 1 should be approximately 0. As delays occur during the surgery, the slope of the expected curve may flatten, e.g., the slope falls below 1. Alternatively, if a portion of the surgery completes more quickly than expected, the slope may get steeper, e.g., the slope increases to greater than 1.

Based on historical predictions during the surgery, the time prediction module 730 may monitor deviations from the expected course of the surgery based on one or more thresholds. For example, the system may identify a delay if the slope of the expected curve drops below 1 by more than a threshold amount, e.g., 20%, for a threshold period of time, e.g., 5 minutes. After one or more thresholds are met, the time prediction module 730 may identify a delay by identifying the time at which the slope deviation beyond the threshold was first detected. Similarly, if the system 700 determines a deviation in area between the expected curve and the reference line increasing from 0 by a threshold amount over a threshold time interval, the time prediction module 730 may identify a delay by identifying the time at which the deviation was first detected. The time prediction module 730 may also access one or more video frames corresponding to the identified time to search for one or more detected activities or events during that time period, e.g., unexpected bleeds, movements, etc.

In addition to analyzing whether a predicted time to completion exceeds a threshold, the system may determine a probability or confidence level that the predicted time-to-complete is accurate, such as based on statistical information about prior procedures. Such statistical information may indicate that apparent delays in a particular surgical phase tend to be bad indicators of an increased time-to-complete for the entire procedure. In some examples, the time prediction module 730 may instead accumulate predicted times to complete over an interval and determine a confidence level based on those predictions based on any suitable statistical analysis or based on the detection of one or more activities or events that may indicate a delay, or the lack thereof, which may indicate a false indication of a delay. Thus, one or more thresholds according to this disclosure may include both a threshold amount of deviation from a reference and a confidence level associated with the deviation.

It should be appreciated that a delay in surgical procedure may result from an event that, once addressed, is eliminated. For example, the expected curve may have a slope of approximately 1 until an event which halts the progress of the surgery for a period of time, e.g., 10 minutes. The event may be a malfunctioning tool for which a replacement is needed, halting the surgery. The slope of the expected curve may then fall to approximately 0 as no progress is made, and then once the tool is replaced, the slope may increase back to approximately 1 again as the surgery continues normally. Thus, a delay may result from a discrete event that may be addressed and the surgery may then resume normally.

However, delays may also occur simply because a surgery is more difficult, e.g., due to idiosyncrasies in a patient's condition, and thus, a delay may be detected relatively early in the surgery because steps of the surgery may take more time than expected. Thus in some cases, the expected curve for the surgery may have an average slope of 0.8 or 0.9 due to the complexity of the particular patient. However, other kinds of delays may still occur during such surgeries, such as due to discrete events, unexpected activities, etc. as discussed above. To detect these further delays, the time prediction module 730 may determine that the expected curve's slope of 0.8 and 0.9 should be the slope for a new reference line for the surgery. For example, over a threshold period of time, the time prediction module 730 may track the expected curve's slope and an amount of deviation from that slope. If the expected curve's slope stays relatively constant, e.g., within a threshold amount of deviation, over that period of time, the time prediction module 730 may begin to adjust the slope of the reference to reduce the deviation between the expected curve and the reference line. The time prediction module 730 may then monitor for further deviations from this new reference based on the thresholds established for the surgical procedure discussed above, e.g., thresholds for deviations from the reference line, time thresholds corresponding to such deviations, etc.

The reference line discussed above may be determined based on information about the surgical procedure obtained from the datastore 740. For example, the system may determine an expected time for the surgical procedure from one or more records in the datastore 740 to establish the reference line. The system 700 may obtain timing information for each phase of the surgical procedure and use the timing information to create reference lines for each phase of the surgical procedure or an aggregate reference line from all of the timing information. It should be appreciated that a reference "line" may not be manifested as a line or other curve per se by the system, but instead may be represented by a number representing a slope, e.g., a value of 1. Thus, if at a particular point in time, the expected time to complete the surgical procedure is 15 minutes, while the predicted time to complete the procedure is 18 minutes, the system 700 may determine a deviation of three minutes, and then may obtain samples of previously predicted times to complete during the surgical procedure to estimate a slope of the expected curve and compare that slope against the slope of the reference line, which is 1 in this example. Thus the system may not actually compute the slope of the reference line, it may simply be established as 1, absent adjustments made to that value during the course of the surgery discussed above.

Further, as discussed above, in some examples, the expected time to complete may be determined based on a statistical distribution, whether a normal distribution or other type of distribution. Further, after a delay has been determined, a new reference may be determined based on similar past surgical procedures and statistical information associated with them. Thus, the new reference may be used for subsequent determinations of delays, which may avoid repeated notifications based on an initial reference expectation that is no longer applicable.

After identifying a delay, the time prediction module 730 may generate metadata identifying the delay, an estimated time during the surgery when the delay occurred (or the time period over which the delay lasted), or one or more activities occurring at approximately the time of the delay being detected or over the course of the delay.

Metadata may be generated to store information relating to delays or events identified during the course of a surgical procedure, and may be associated with video captured during the surgical procedure to enable efficient access to portions of the video corresponding to identified delays, activities, events, etc. In this example, the estimated time remaining information 732 or the delay notification 734 generated by the time prediction module 730 may be stored as metadata by the system 700, such as in a datastore (e.g., datastore 740), as metadata within a video file, or in one or more separate files.

Generated metadata may include time information, such as the time at which a delay was identified, the estimated time at which an event or activity caused a delay, a corresponding event (e.g., unexpected bleeding) or activity (e.g., incision), information about a surgeon (e.g., surgeon commanding the surgical robot) or the type of surgical procedure, etc. The generated metadata may then be associated with the surgical procedure or with video associated with the surgical video, such as video captured by an endoscopic camera. As discussed above, a surgical robot may capture video during the surgical video, and the system 700 may associated generated metadata with the captured video.

To assist a user who later searches for or watches a surgical video, metadata may be provided in the form of bookmarks within a video file, or other information, such as annotations. Metadata may be stored in any suitable format, such as using tags, e.g., via extensible markup language ("XML"), or other escape characters or sequences to delineate annotations or metadata from video content. At a later time, when a user accesses a surgical video with associated annotations and begins to watch it, she may be presented with the bookmarks, commentary, or other relevant information to enable the user to identify a video of interest, e.g., via search functionality based on the metadata, or to jump to particular points within the video, e.g., to view activities or events that were associated with a detected delay in the surgical procedure. In some examples, the metadata may include information identifying the typical timeline of the type of surgical procedure as compared to the timeline of the surgical procedure depicted in the video. For example, the video may include annotations identifying different phases of the surgical procedure, and at a change to a new phase, may indicate a time difference between a typical timeline and the timeline of the surgical procedure depicted in the video. Similarly, the metadata may illustrate a graphical comparison of the two timelines, such as the example comparison depicted in FIG. 8.

Figure 8:
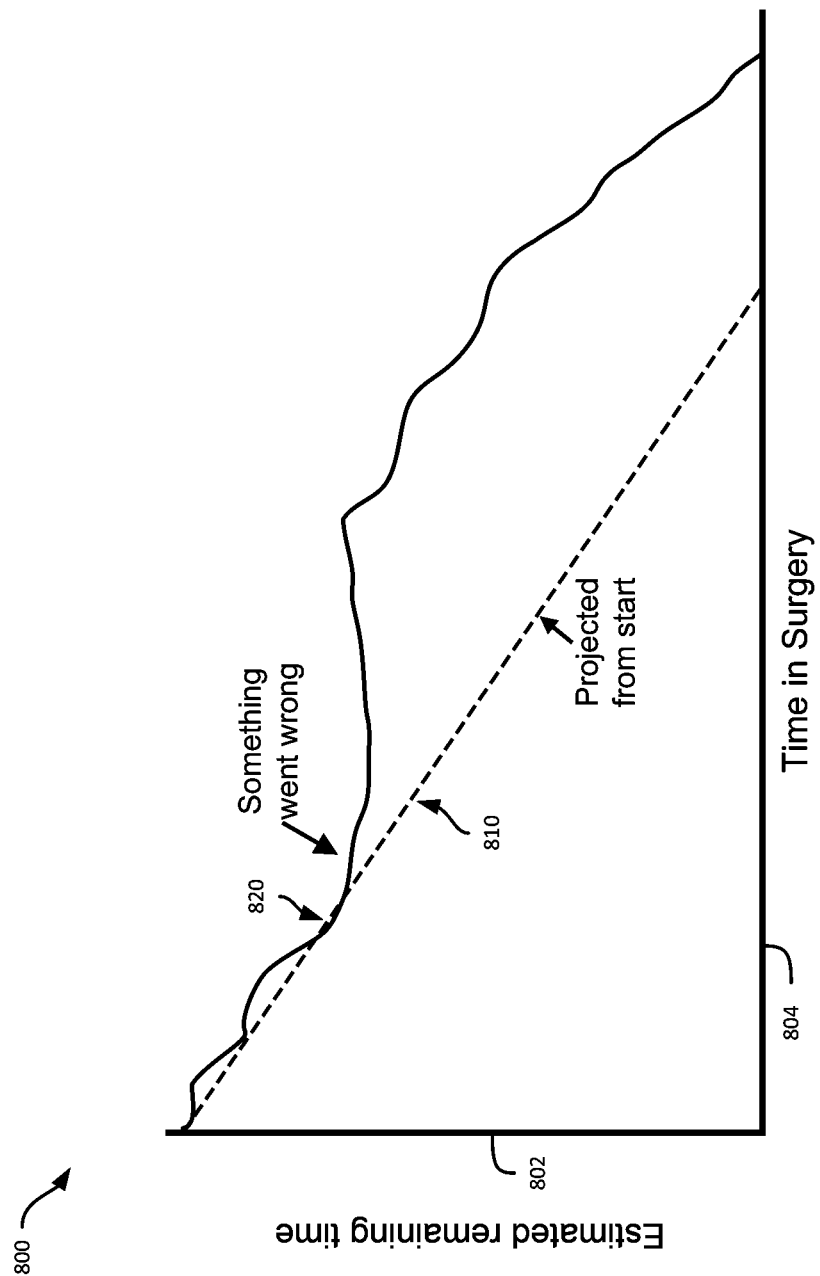
FIG. 8 illustrates an example comparison between two timelines represented with respect to two axes.

FIG. 8 illustrates an example comparison 800 between two timelines 810, 820 represented with respect to two axes 802, 804, where the vertical axis represents the estimated time remaining in a surgical procedure, while the horizontal axis represents the actual elapsed time in surgery. The depicted timelines represent the estimated time remaining in a typical surgical procedure 810 and the estimated time remaining the surgical procedure depicted in the video 820. Such a representation clearly illustrates divergence of timeline 820 from timeline 810 and indicates a delay. In some examples, the timeline 820 may be represented by metadata, e.g., timestamps within the timeline may be correlated to frames within the video, that is usable to scrub through the video. Thus, a user could quickly scrub to a point on the timeline 820 of interest and view the video and the potential cause of the delay, even if no other metadata identifying activities or events was provided. In some examples, such a timeline may also provide annotations, such as text or selectable points or segments that trigger a display of textual, audio, or video annotations corresponding to a particular frame or segment of the video when selected.

Referring again to FIG. 7, because video data may be stored in real-time as it is being captured, but activity or delay detection may occur at a later time, the system 700 may generate timestamps for expected delays based on a system clock or other reference time base. The system 700 may also associate the time at which video recording began to the reference time base to enable later correlations between detected events, activities, or delays with particular frames or groups of frames within the recorded video. Information about the reference time base may be included with the metadata. Alternatively, relative times from the first frame of the recorded video may be calculated based on the reference time base and frame rate and then associated with metadata to enable correlation between metadata entries and one or more frames of a corresponding video. Further, the metadata may later be incorporated into the stored video, such as through the use of tags or other metadata format supported by a relevant video encoding standard.

Figure 9:
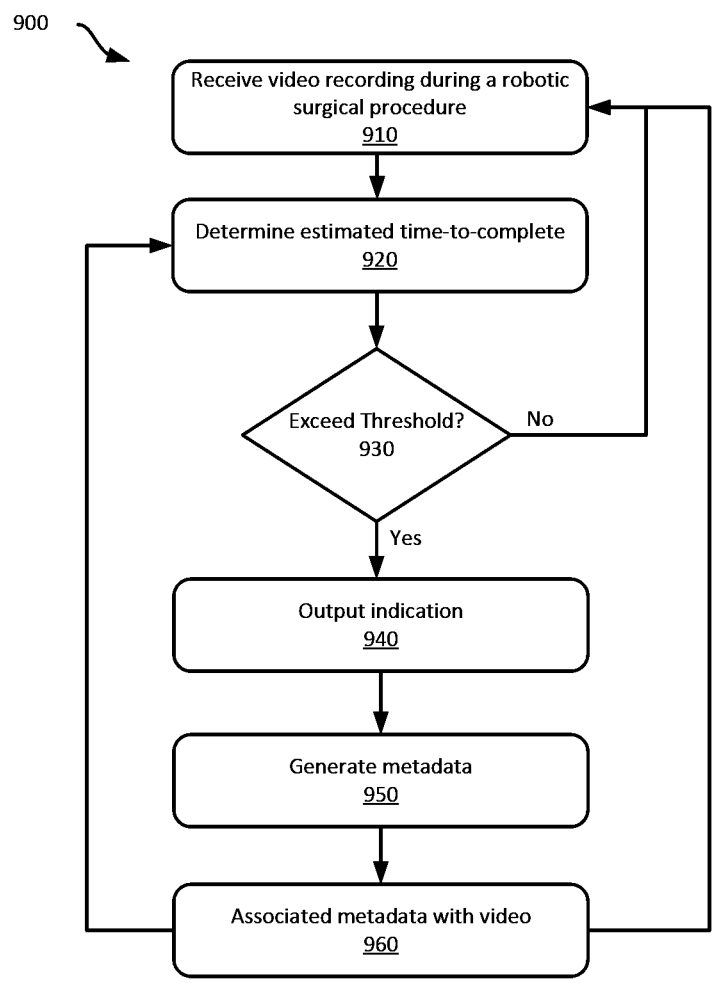
FIG. 9 shows an example method for detecting deviations from an expected duration of a surgical procedure.

Referring now to FIG. 9, FIG. 9 shows an example method 900 for detecting deviations from an expected duration of a surgical procedure according to this disclosure. The method will be described with respect to the system 700 shown in FIG. 7, however, it should be appreciated that this and other example methods according to this disclosure may be performed by any suitable system according to this disclosure.

At block 910, the system 700 receives video of a robotic surgical procedure. As discussed above, the system 700 may receive the video in real-time as the robotic surgical video is recorded, such as from an endoscope. In some examples, the video may be retrieved from a storage medium, such as a local memory device within the system 700 or from a remote storage medium, such as at a remote server or from a remote datastore. Further, it should be appreciated that a video of a surgical procedure may include multiple discrete videos that collectively represent the surgical procedure. For example, a surgical procedure may take many hours to complete, and thus video of the surgical procedure may be segmented into multiple discrete video files. Alternatively, multiple videos may be recorded of a surgical procedure due to the use of multiple different cameras during the surgical procedure. For example, the surgical procedure may be recorded by an endoscope as well as a camera positioned externally to the patient and oriented to capture video of the patient during the surgery.

At block 920, the system 700 determines a time-to-complete the surgical procedure at a particular frame or series of frames of the video. In this example, the system 700 first employs the video analysis module 720 to first identify activities or events occurring during the surgical procedure and phases of the surgical procedure. When the video is received in real-time from a camera, such as an endoscope, the video analysis module 720 may make determinations about then-current activities, events, or phase of the surgical procedure based on received frames of the video, and store such determinations in a storage medium and continue to perform such analyses during the course of the surgical procedure as video is received. If the video has previously been recorded, the video analysis module 720 may be provided with one or more frames sampled from the stored video. The video analysis module 720 then processes the provided frames to make determinations about then-current activities, events, or phase of the surgical procedure.

After determining activities, events, or phase information, the system 700 employs the time prediction module 730 to determine an estimated time remaining 732 in the surgical procedure. As discussed above, the time prediction module 730 may access information stored in the datastore 740 that indicates an expected time to complete the surgical procedure, expected times to complete different phases of the surgical procedure, expected activities or events during one or more phases of the surgical procedure, etc. The time prediction module 730 may then use such information to determine an expected time to complete based on the determined then-current phase of the surgical procedure, e.g., as determined by the video analysis module 720, one or more detected activities or events within the video, etc. generally as described above with respect to FIG. 7. The time prediction module 740 may then output an estimated time remaining 732 in the surgical procedure, the phase of the surgical procedure, etc.

It should be appreciated that block 920 may occur repeatedly over the course of a surgical video. For example, if a video is received in real-time, e.g., from a camera during surgery, the system 700 may sample each video frame, sample only a subset of video frames to process, or it may sample video frames at a predetermined rate, e.g., one frame per second. The system 700 may then process one or more sampled video frame using the video analysis module 720 and the time prediction module 730. Further, results from processing multiple frames of video may be employed to determine activities, events, or phase information, generally as discussed above with respect to FIGS. 2-6B. For example, phase information determined from multiple frames may be used to determine a likelihood that the surgery is in a particular phase. Similarly, activity or event information determined from multiple frames may be used to determine a likelihood that the identified activity or event occurred.

For example, each frame may be scored with a value, e.g., between 0 and 1, indicating a likelihood that a particular activity or event is present in the frame. Then, scores from multiple frames in temporal proximity with each other may have their scores compared to determine if the event or activity is detected, e.g., using a "majority rules" technique or by averaging the values for each frame and comparing against a threshold. For example, if 10 frames are analyzed and 8 indicate the event occurred and 2 indicated the event did not occur, the system may determine that the event occurred because the majority of the frames indicate the event occurred.

At block 930, the system 700 determines whether the time-to-complete exceeds a threshold deviation from the expected time-to-complete the surgical procedure. As discussed above with respect to FIG. 7, the system 700 can track the elapsed time in the procedure and, based on the total expected time of the procedure, determine the expected remaining time should be. It can then compare the expected remaining time with the determined time-to-complete to determine a difference between the two. If the difference exceeds the threshold, the method 900 proceeds to block 940. Similarly, the system 700 may determine a deviation from the expected course of surgery as discussed above with respect to system 700 by determining a slope of a curve based on the successive predicted times-to-complete and compare the slope of that curve with an expected slope for the surgical procedure or the then-current phase of the surgical procedure. Still further techniques, such as those discussed above, may be used to determine whether the time-to-complete exceeds a threshold. However, if the time-to-complete is within the threshold, the method 900 may return to block 910 and continue to receive video of the robotic surgical procedure.

It should be appreciated that, while discussion herein has related to surgical procedures taking longer than expected, in some examples, the system 700 may also determine whether the expected time-to-complete the surgical procedure is less than the expected time by a threshold amount, e.g., 10%. Such a determination may be used to help identify surgical procedures in which the surgeon was particularly efficient, e.g., when a different surgical technique was used that led to a faster completion time. Further, as discussed elsewhere, such information may be used to provide notifications to personnel that a procedure is on an accelerated schedule, a scheduled action, e.g., anesthesia or assistance from an attending physician, may be moved up in time, etc.

At block 940, the system 700 outputs a delay indication. In this example a delay indication includes an indication that the surgical procedure will take longer than expected. For example, the system 700 may output a graphical indication of the expected time remaining in the surgical procedure or the elapsed time of the surgical procedure, and change the color of a displayed elapsed or remaining time based on the presence or absence of a delay, e.g., the time indication may be white or green if the surgery appears to be on schedule and may change to yellow or red if a delay is detected. Further, the color of the time indication may change based on the amount of the delay, e.g., a 10% increase in the projected time to complete may cause the time indication to display as yellow, and it may change to red if the expected delay increases to 50% or more than the originally expected time to complete the surgery. Still further color changes may be employed.

The delay indication may include additional or other information in some examples. A delay indication may identify the time at which the delay was first detected or the system 700 may identify an activity or event that likely caused the delay, such as discussed above with respect to FIG. 7.

To output the delay notification, the system 700 may provide a visual or audible indication of the delay, such as the time indications discussed above. The system 700 may output an indication of the expected completion time of the procedure based on the delay or it may output an amount of time by which the procedure was delayed, e.g., 30 minutes. Further, the system 700 may output a notification to members of the surgical team, administrative staff, family members of the patient, or other personnel at the medical center where the operation is being performed.

For example, the system 700 may cause a text message, page, email, etc. to be transmitted to one or more such people. It may be desirable to notify a surgeon about a delay in the surgical procedure if the surgeon is scheduled to assist the surgery at a particular phase of the surgery. This can help eliminate wasting any of the surgeon's time, e.g., by preventing the surgeon from arriving too early. Similarly, such information may be useful to an administrator who schedules surgeries. If a delay notification is provided to the administrator, she may be able to adjust the schedules of later surgeries or to notify surgical personnel that their scheduled procedure may start later than expected. Still other types of notifications may be output according to different examples.

At block 750, the system 700 generates metadata based on the detected delay. As discussed above with respect to FIG. 7, metadata may be generated identifying the time of the delay, a time at which the timeline of the surgical procedure begins to deviate from the expected timeline by a threshold amount, an activity or event associated with the delay, e.g., such an activity or event that occurred shortly before or at about the time the delay was detected. In some examples, the system may determine a frame or sequence of frames within the video corresponding to the detected delay or an associated activity or event, and generate metadata identifying the frame or sequence of frames.

As discussed above with respect to FIG. 7, metadata may be generated in any suitable format, such as using XML or generating annotations within a video file. Metadata may be generated by the time prediction module 730 or the processor may execute other processor-executable instructions to generate the metadata.

At block 760, the generated metadata is associated with the video. For example, the system 700 may generate a metadata file that includes information identifying a video, such as by file name, patient name, date and time of the surgery, the medical center, members of the surgical staff, or one or more unique identifiers (e.g., a patient ID number or a surgery ID number). Such a file may include such information as well as one or more references to one or more frames or times within the video. For example, the system may reference a specific frame number in the video or it may include an elapsed time within the video, e.g., 4 minutes 47 seconds from the beginning of the video. In some examples, the metadata may be incorporated into the video file, such as by including metadata identifying one or more frames of the video associated with the identified delay. Further, the metadata may identify one or more bookmarks within the video and may include textual information describing the bookmark or providing an overlay on the video during playback of the relevant frame or frames of the video.

After completing block 760, the method returns to block 910, or if the system is analyzing previously recorded video, it may return instead to block 920. It should be appreciated that the system 700 may execute the method in any order, may perform multiple blocks simultaneously, or may omit one or more blocks. For example, the system 700 may receive video frames 910 in real time, e.g., at 24 or 30 frames per second, but may execute other blocks, e.g., 920, at a slower rate, e.g., the video analysis module or the time prediction module may run at 1 frame per second. Further, it should be appreciated that blocks 950 or 960 may be omitted in some examples. For example, a suitable system according to this disclosure may output delay indications, but may not generate metadata to be associated with the video. Instead, the system may simply operate to notify the surgical team, the medical center staff, or the patient's staff, etc. of delays encountered during a surgical procedure without also generating metadata or associating it with the recorded video.

Figure 10:
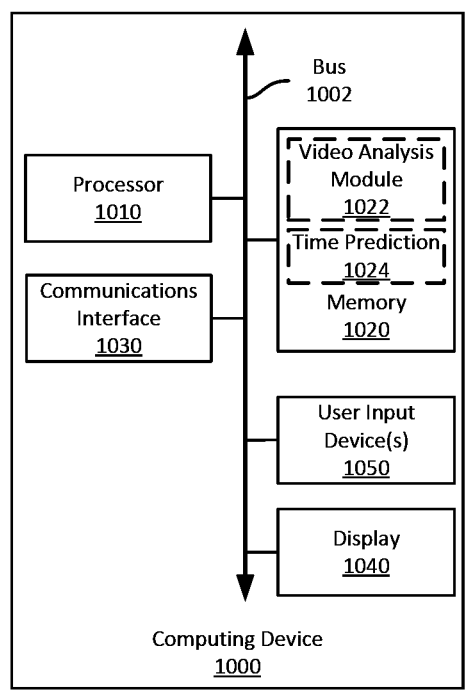
FIG. 10 illustrates an example computing device 1000 suitable for use with systems and methods for detecting delays during a surgical procedure according to this disclosure.

Referring now to FIG. 10, FIG. 10 illustrates an example computing device 1000 suitable for use with systems and methods for detecting delays during a surgical procedure according to this disclosure. The example computing device 1000 includes a processor 1010 which is in communication with the memory 1020 and other components of the computing device 1000 using one or more communications buses 1002. The processor 1010 is configured to execute processor-executable instructions stored in the memory 1020 to perform one or more methods for detecting delays during a surgical procedure according to different examples, such as part or all of the example method 900 described above with respect to FIG. 9. In this example, the memory 1020 stores processor-executable instructions that provide a video analysis module 1022 and a time prediction module 1024, such as those discussed above with respect to FIG. 7. The computing device, in this example, also includes one or more user input devices 1050, such as a keyboard, mouse, touchscreen, microphone, etc., to accept user input. The computing device 1000 also includes a display 1040 to provide visual output to a user.

The computing device 1000 also includes a communications interface 1040. In some examples, the communications interface 1030 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
receiving, by a computing device, video of a robotic surgical procedure;
determining, by the computing device, an estimated time-to-complete ("TTC") the robotic surgical procedure based on the video; and
in response to determining that a deviation exceeds a threshold, the deviation between the estimated TTC and an expected duration of the robotic surgical procedure:
determining one or more frames in the video, the one or more frames corresponding to an initial time of the deviation between the estimated TTC and the expected duration;
outputting an indication that the robotic surgical procedure is deviating from the expected duration; and
outputting an identification of the one or more frames corresponding to the initial time of the deviation.

2. The method of claim 1, further comprising:
generating metadata corresponding to the one or more frames indicating the initial time of the deviation; and
associating the metadata with the video.

3. The method of claim 2, wherein the metadata comprises a bookmark.

4. The method of claim 2, further comprising determining a step of the robotic surgical procedure corresponding to the one or more frames.

5. The method of claim 1, wherein receiving the video occurs in real-time during the robotic surgical procedure.

6. The method of claim 5, wherein outputting the indication comprises displaying a graphical indication of the deviation.

7. The method of claim 5, wherein outputting the indication comprises transmitting a message to a remote computing device associated with medical personal, the message indicating the deviation.

8. The method of claim 7, wherein the transmitting the message comprises sending a text message to a mobile device.

9. The method of claim 1, wherein receiving the video comprises receiving the video from a storage device.

10. A non-transitory computer-readable medium comprising processor-executable instructions configured to cause a processor to:
receive video of a robotic surgical procedure;
determine an estimated time-to-complete ("TTC") the robotic surgical procedure based on the video; and
in response to a determination that a deviation exceeds a threshold, the deviation between the estimated TTC and an expected duration of the robotic surgical procedure:
determine one or more frames in the video, the one or more frames corresponding to an initial time of the deviation between the estimated TTC and the expected duration;
output an indication that the robotic surgical procedure is deviating from the expected duration; and
outputting an identification of the one or more frames corresponding to the initial time of the deviation.

11. The non-transitory computer-readable medium of claim 10, further comprising processor-executable instructions configured to cause a processor to:
generate metadata corresponding to the one or more frames indicating the initial time of the deviation; and
associate the metadata with the video.

12. The non-transitory computer-readable medium of claim 11, wherein the metadata comprises a bookmark.

13. The non-transitory computer-readable medium of claim 11, further comprising processor-executable instructions configured to cause a processor to determine a step of the robotic surgical procedure corresponding to the one or more frames.

14. The non-transitory computer-readable medium of claim 10, further comprising processor-executable instructions configured to cause a processor to receive the video in real-time during the robotic surgical procedure.

15. The non-transitory computer-readable medium of claim 14, further comprising processor-executable instructions configured to cause a processor to display a graphical indication of the deviation.

16. The non-transitory computer-readable medium of claim 14, further comprising processor-executable instructions configured to cause a processor to transmit a message to a remote computing device associated with medical personal, the message indicating the deviation.

17. The non-transitory computer-readable medium of claim 16, further comprising processor-executable instructions configured to cause a processor to send a text message to a mobile device.

18. The non-transitory computer-readable medium of claim 10, further comprising processor-executable instructions configured to cause a processor to receive the video from a storage device.

19. A computing device comprising:
a non-transitory computer-readable medium; and
a processor communicatively coupled to the non-transitory computer-readable medium, the processor configured to execute processor-executable instructions stored in the non-transitory computer-readable medium to:
receive video of a robotic surgical procedure;
determine an estimated time-to-complete ("TTC") the robotic surgical procedure based on the video; and
in response to a determination that a deviation exceeds a threshold, the deviation between the estimated TTC and an expected duration of the robotic surgical procedure:
determine one or more frames in the video, the one or more frames corresponding to an initial time of the deviation between the estimated TTC and the expected duration, the initial time of the deviation based on a difference between the estimated TTC and an expected TTC being within a threshold difference;
output an indication that the robotic surgical procedure is deviating from the expected duration; and
outputting an identification of the one or more frames corresponding to the initial time of the deviation.

20. The computing device of claim 19, wherein the processor is configured to execute processor-executable instructions stored in the non-transitory computer-readable medium to cause a processor to:
determine one or more frames in the video, the one or more frames corresponding to an initial time of the deviation between the estimated TTC and the expected duration;
generate metadata corresponding to the one or more frames indicating the initial time of the deviation; and
associate the metadata with the video.

21. The computing device of claim 20, wherein the metadata comprises a bookmark.

22. The computing device of claim 20, wherein the processor is configured to execute processor-executable instructions stored in the non-transitory computer-readable medium to cause a processor to determine a step of the robotic surgical procedure corresponding to the one or more frames.

23. The computing device of claim 19, wherein the processor is configured to execute processor-executable instructions stored in the non-transitory computer-readable medium to cause a processor to receive the video in real-time during the robotic surgical procedure.

24. The computing device of claim 23, wherein the processor is configured to execute processor-executable instructions stored in the non-transitory computer-readable medium to cause a processor to display a graphical indication of the deviation.

25. The computing device of claim 23, wherein the processor is configured to execute processor-executable instructions stored in the non-transitory computer-readable medium to cause a processor to transmit a message to a remote computing device associated with medical personal, the message indicating the deviation.

26. The computing device of claim 25, wherein the processor is configured to execute processor-executable instructions stored in the non-transitory computer-readable medium to cause a processor to send a text message to a mobile device.

27. The computing device of claim 19, wherein the processor is configured to execute processor-executable instructions stored in the non-transitory computer-readable medium to cause a processor to receive the video from a storage device.

* * * * *